(12) United States Patent
Coull et al.

(10) Patent No.: US 8,187,823 B2
(45) Date of Patent: May 29, 2012

(54) MODULATION OF NEUROGLIA-DERIVED BDNF IN THE TREATMENT AND PREVENTION OF PAIN

(75) Inventors: Jeffrey A. M. Coull, Toronto (CA); Yves De Koninck, Ste-Foy (CA); Michael Salter, Toronto (CA); Simon Beggs, Toronto (CA)

(73) Assignees: Université Laval (CA); The Hospital for Sick Children (CA)

( * ) Notice: Subject to any disclaimer, the term of this patent is extended or adjusted under 35 U.S.C. 154(b) by 411 days.

(21) Appl. No.: 11/665,934

(22) PCT Filed: Sep. 30, 2005

(86) PCT No.: PCT/CA2005/001501
§ 371 (c)(1),
(2), (4) Date: Oct. 10, 2008

(87) PCT Pub. No.: WO2006/042396
PCT Pub. Date: Apr. 27, 2006

(65) Prior Publication Data
US 2009/0227654 A1 Sep. 10, 2009

Related U.S. Application Data

(60) Provisional application No. 60/620,722, filed on Oct. 22, 2004.

(51) Int. Cl.
*G01N 33/567* (2006.01)
*C07H 21/02* (2006.01)
*C07K 1/00* (2006.01)

(52) U.S. Cl. ........................ 435/7.21; 536/24.5; 530/350
(58) Field of Classification Search .................. None
See application file for complete search history.

(56) References Cited

FOREIGN PATENT DOCUMENTS
WO  WO-2005/059135 A2  6/2005

OTHER PUBLICATIONS

Rose et al (Nature 426: 74-78, 2003).*
Groth et al (Pain 100: 171-181, 2002).*
"European Patent Application Serial No. EP 05792071.2, European Search Report mailed Jan. 16, 2009", 10 pgs.
Baker-Herman, T. L., et al., "BDNF is necessary and sufficient for spinal respiratory plasticity following intermitten hypoxia", *Nature Neuroscience*, 7(1), (2004), 48-55.
Balkowiec, A., et al., "Activity-Dependent Release of Endogenous Brain-Derived Neurotrophic Factor from Primary Sensory Neurons Detected by ELISA In Situ", *The Journal of Neuroscience*, 20(19), (2000), 7417-7423.
Chaplan, S. R., et al., "Quantitative assessment of tactile allodynia in the rat paw", *Journal of Neuroscience Methods*, 53, (1994), 55-63.
Chen, G., et al., "Relative Contribution of Endogenous Neurotrophins in Hippocampal Long-Term Potentiation", *The Journal of Neuroscience*, 19(18), (1999), 7983-7990.
Chéry, N., et al., "Visualization of lamina I of the dorsal horn in live adult rat spinal cord slices", *Journal of Neuroscience Methods*, 96, (2000), 133-142.
Coderre, T. J., et al., "The Contribution of Excitatory Amino Acids to Central Sensitization and Persistent Nociception after Formalin-induced Tissue Injury", *The Journal of Neuroscience*, 12(9), (1992), 3665-3670.
Coull, J. A. M., et al., "Trans-synaptic shift in anion gradient in spinal lamina I neurons as a mechanism of neuropathic pain", *Nature*, 424, (2003), 938-942.
Dougherty, K. D., et al., "Brain-Derived Neurotrophic Factor in Astrocytes, Oligodendrocytes, and Microglia/Macrophages after Spinal Cord Injury", *Neurobiology of Disease*, 7, (2000), 574-585.
Gravel, C., et al., "Adenoviral gene transfer of ciliary neurotrophic factor and brain-derived neurotrophic factor leads to long-term survival of axotomized motor neurons", *Nature Medicine*, 3(7), (1997), 765-770.
Ha, S. O., et al., "Expression of brain-derived neurotrophic factor in rat dorsal root ganglia, spinal cord and gracile nuclei in experimental models of neuropathic pain", *Neuroscience*, 107(2), (2001), 301-309.
Heppenstall, P. A., et al., "BDNF but not NT-4 is required for normal flexion relfex plasticity and function", *Proc. Natl. Acad. Sci. USA*, 98(14), (2001), 8107-8112.
Jiang, B., et al., "Long-Term Depression is Not Induced by Low-Frequency Stimulation in Rat Visual Cortex In Vivo: A Possible Preventing Role of Endogenous Brain-Derived Neurotrophic Factor", *The Journal of Neuroscience*, 23(9), (2003), 3761-3770.
Keller, A. F., et al., "Region-Specific Development Specialization of GABA-Glycine Cosynapses in Laminas I-II of the Rat Spinal Dorsal Horn", *The Journal of Neuroscience*, 21(20), (2001), 7871-7880.
Kerr, B. J., et al., "Brain-Derived Neurotrophic Factor Modulates Nociceptive Sensory Inputs and NMDA-Evoked Responses in the Rat Spinal Cord", *The Journal of Neuroscience*, 19(12), (1999), 5138-5148.
Lever, I. J., et al., "Brain-Derived Neurotrophic Factor is Released in the Dorsal Horn by Distinctive Patterns of Afferent Fiber Stimulation", *The Journal of Neuroscience*, 21(12), (2001), 4469-4477.
Malcangio, M., et al., "A common thread for pain and memory synapses? Brain-derived neurotrophic factor and trkB receptors", *TRENDS in Pharmacological Sciences*, 24(3), (2003), 116-121.
Mannion, R. J., et al., "Neurotrophins: Peripherally and centrally acting modulators of tactile stimulus-induced inflammatory pain hypersensitivity", *Proc. Natl. Acad. Sci. USA*, 96, (1999), 9385-9390.
Miletic, G., et al., "Increases in the concentration of brain derived neurotrophic factor in the lumbar spinal dorsal horn are associated with pain behavior following chronic constriction injury in rats", *Neuroscience Letters*, 319(3), (2002), 137-140.
Morigucha, S., et al., "Potentiation of NMDA receptor-mediated synaptic responses by microglia", *Molecular Brain Research*, 119, (2003), 160-169.

(Continued)

Primary Examiner — Richard Schnizer
(74) Attorney, Agent, or Firm — Schwegman, Lundberg & Woessner, P.A.

(57) ABSTRACT

Methods and products for the attenuation or treatment of pain and the reduction of nociception are described. The methods and products are based on the modulation of neuroglia-derived BDNF expression or activity. Also described herein are commercial packages and uses based on such modulation. Related methods for identifying or characterizing compounds for the treatment of pain and the reduction of nociception are also described.

6 Claims, 12 Drawing Sheets

OTHER PUBLICATIONS

Mosconi, T., et al., "Fixed-diameter polyethylene cuffs applied to the rat sciatic nerve induce a painful neuropathy: ultrastructural morphometric analysis of axonal alterations", *Pain*, 64, (1996), 37-57.

Nakajima, K., et al., "Ceramide activates microglia to enhance the production/secretion of brain-derived neurotrophic factor (BDNF) without induction of delterious factors in vitro", *Journal of Neurochemistry*, 80, (2002), 697-705.

Nakajima, K., et al., "Identification of Elastase as a Secretory Protease from Cultured Rat Microglia", *Journal of Neurochemistry*, 58, (1992), 1401-1408.

Rivera, C., et al., "BDNF-induced TrkB activation down-regulates the $K^+$-$Cl^-$ cotransporter KCC2 and impairs neuronal $Cl^-$ extrusion", *The Journal of Cell Biology*, 159(5), (2002), 747-752.

Skup, M., et al., "Long-Term Locomotor Training Up-Regulates $TrkB^{FL}$ Receptor-like Proteins, Brain-Derived Neurotrophic Factor, and Neurotrophin 4 with Different Topographies of Expression in Oligodendroglia and Neurons in the Spinal Cord", *Experimental Neurology*, 176, (2002), 289-307.

Thompson, S. W. N., et al., "Brain-derived neurotrophic factor is an endogenous modulator of nociceptive responses in the spinal cord", *Proc. Natl. Acad. Sci. USA*, 96, (1999), 7714-7718.

Tyzio, R., et al., "Membrane Potential of CA3 Hippocampal Pyramidal Cells During Postnatal Development", *J. Neurophysiol.*, 90, (2003), 2964-2972.

Wardle, R. A., et al., "Brain-Dervived Neurotrophic Factor Modulation of GABAergic Synapses by Postsynaptic Regulation of Chloride Transport", *The Journal of Neuroscience*, 23(25), (2003), 8722-8732.

Woolf, C. J., et al., "Neuronal Plasticity: Increasing the Gain in Pain", *Science*, 288, (2000), 1765-1768.

Yajima, Y., et al., "Involvement of a spinal brain-derived neurotrophic factor/full-length TrkB pathway in the development of nerve injury-induced thermal hyperalgesia in mice", *Brain Research*, 958(2), (2002), 338-346.

Yaksh, T. L., et al., "Intrathecal morphine inhibits substance P release from mammalian spinal cord in vivo", *Nature*, 286, (1980), 155-157.

Zhang, J., et al., "Neurotrophins regulate proliferation and survival of two microglial cell lines in vitro", *Experimental Neurology*, 183(2), (2003), 469-481.

Zhou, X.-F., et al., "Neurotrophins from dorsal root ganglia trigger allodynia after spinal injury in rats", *European Journal of Neuroscience*, 12(1), (2000), 100-105.

International Preliminary Report on Patentability mailed Apr. 24, 2007 in corresponding PCT Application No. PCT/CA2005/001501, 6 pgs.

International Search Report mailed Jan. 12, 2006 in corresponding PCT Application No. PCT/CA2005/001501, 3 pgs.

Dorn, G., et al., "siRNA Relieves Chronic Neuropathic Pain", *Nucleic Acids Research*, 32(5), (2004),6 pgs.

Groth, R., et al., "Spinal Brain-Derived Neurotrophic Factor (BDNF) Produces Hyperalgesia in Normal Mice While Antisense Directed Against Either BDNF or trkB, Prevent Inflammation-Induced Hyperalgesia", *Pain*, 100(1), (Nov. 2002), 171-181.

Rose, C. R., et al., "Truncated TrkB-T1 Mediates Neurotrophin-Evoked Calcium Signalling in Glia Cells", *Nature*, 426(6962), (2003), 74-78.

Tsuda, M., et al., "$P2X_4$ Receptors Induced in Spinal Microglia Gate Tactile Allodynia After Nerve Injury", *Nature*, 424(6950), (2003), 778-783.

"International Application Serial No. PCT/CA2005/001501, International Preliminary Report on Patentability mailed May 3, 2007", 8 pgs.

"Japanese Application No. 2007-537080, English Translation of Notice of Reasons for Rejection mailed Sep. 14, 2010", 8 pgs.

Alderson, Ralph F., et al., "Truncated TrkB mediates the endocytosis and release of BDNF and neurotrophin-4/5 by rat astrocytes and Schwann cells in vitro", Brain Research, vol. 871, (2000), 210-222.

Fukuoka, Tetsuo, et al., "Brain-Derived Neurotrophic Factor Increases in the Uninjured Dorsal Root Ganglion Neurons in Selective Spinal Nerve Ligation Model", The Journal of Neuroscience, vol. 21, No. 13, (2001), 4891-4900.

Inoue, Kazuhide, et al., "Progress in Medicine, vol. 209, No. 11," (Jun. 2004), 906-907.

Ueda, Hiroshi, "Pain and QOL-morphine-tolerance and morphine-resistant neuropathic pain", Folia Pharmacol. Jpn, vol. 122, (2003), 192-200.

\* cited by examiner

FIG. 2A  FIG. 2B

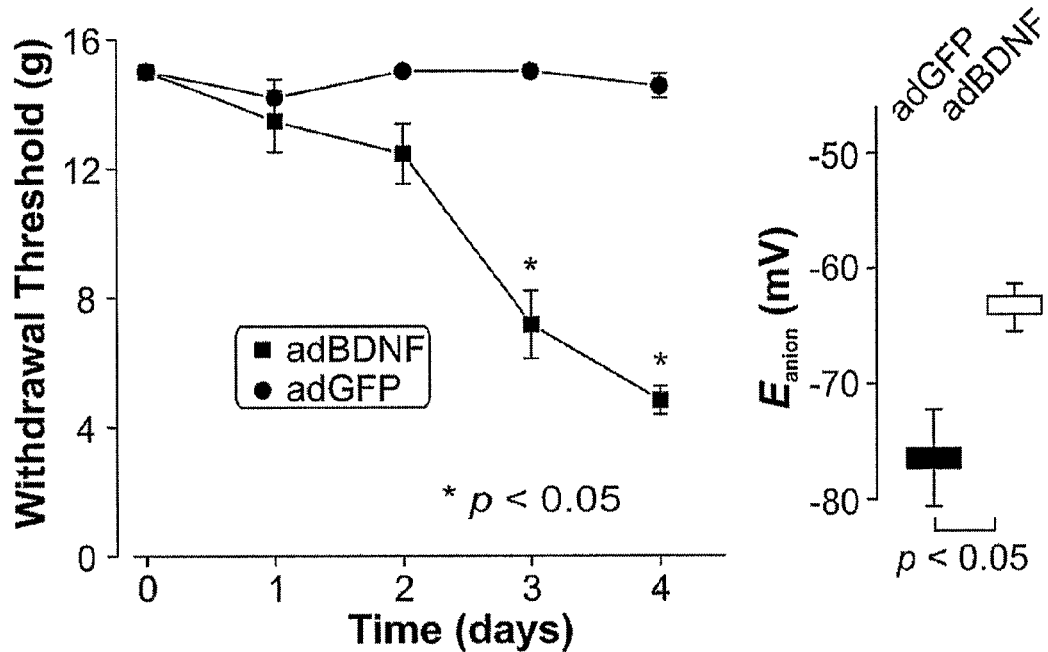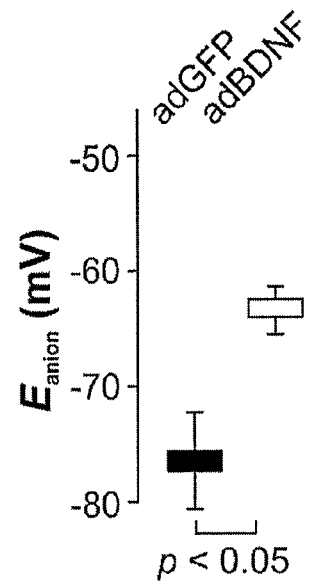
FIG. 2D          FIG. 2E
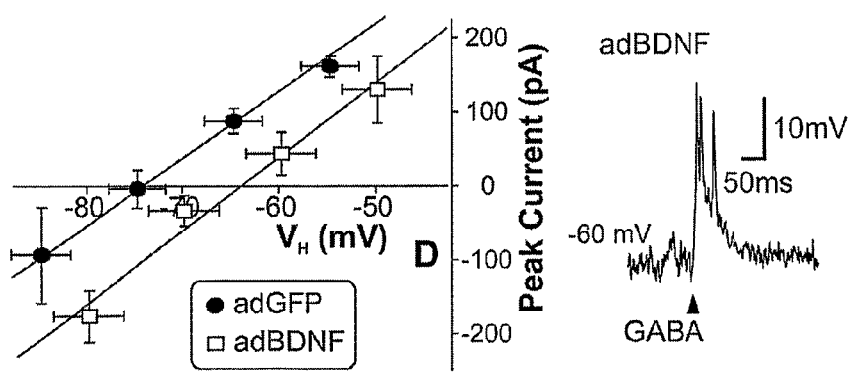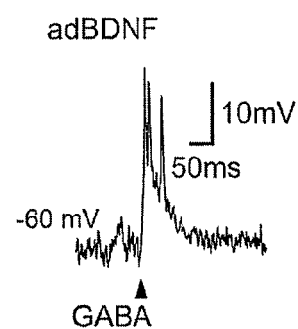
FIG. 2F          FIG. 2G

FIG. 3A  FIG. 3B

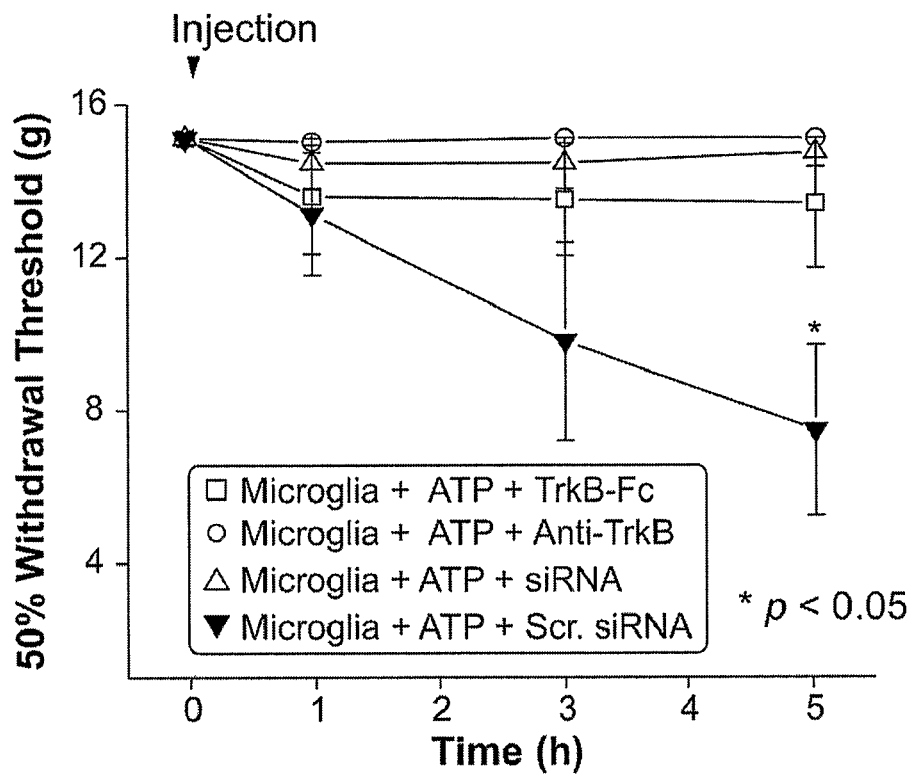
FIG. 4A
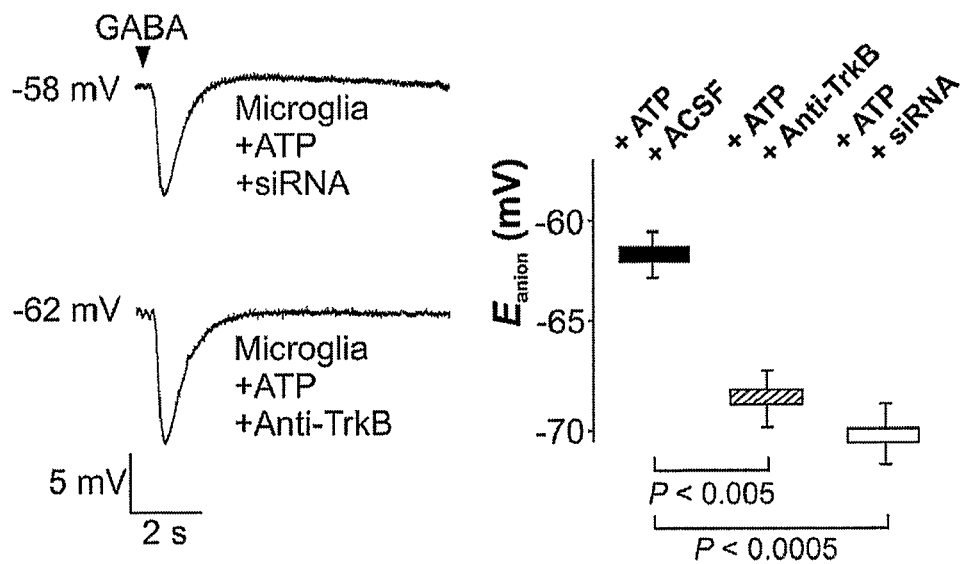
FIG. 4B  FIG. 4C

Coding sequence for Homo sapiens BDNF (SEQ ID NO: 1, Accession number M37762)

>gi|179402|gb|M37762.1|HUMBDNF Human brain-derived neurotrophic factor (BDNF) gene, complete cds
GGTGAAAAGAAGCCCTAACCAGTTTTCTGTCTTGTTTCTCTTCCCTACAGTTCCACCAGGTGAGAA
GAGTGATGACCATCCTTTTCCTTACTATGGTTATTTCATACTTTGGTTGCGGACTCTGCCCATGAA
AGAAGCAAACATCCGAGGACAAGGTGGCTTGCCCTTGGAGAGCAGTGGCGGACACACTTGACTGAG
GTGAATGGGCCCAAGGCAGGTTCAAGAGGCTTGACATCATTGGCTGACACACTTCGAACACGTGAT
AGCTGGTGATGATGCTCAGTAGTCAAGTGCCTTTGGAGCCTCCTCTTCTGCTGGTACACGTC
CAGGGGTGATGCTCAGCAGTCAACTGTCCATGGGGTCCCGTGAAAAGGCCAACTGAAAAGAGAAAT
TACCTAGATGCTGCACAGTATTAGTGAGTCCATGGGTCCCGTATCAAAAGACTGAAGCAAAAGCCA
GCGTGTGTGACAGTTCCCTGAAAAGGTCACACGTGCGGGCAAGGGGCATAGCAGTCAAAAGGAGAA
GACGGTCAATCCCAGTCGTACGTGTGTACAGTCGCGGGCCCTTACCATTGACCATTAAAAGGGGAA
TGCAATACCCAGTCTTCTTGTGTATGTACAAAAATTATCTATTTGTATATATCATAAAGAGATAGT
GAACTACCCAGTCTTCTTGTGTATGTACAAAAATTATCTATTTGTATATATACATAACAGGGGTA
AATTATTCAGTTAAGAAAA
AATAAT Polypeptide sequence of Homo sapiens BDNF (SEQ ID NO: 2, Accession number AAA51820)

>gi|179403|gb|AAA51820.1| brain-derived neurotrophic factor
MTILFLTMVISYFGCMKAAPMKEANIRGQGGLAYPGVRTHGTLESVNGPKAGSRGLTSLADTFEHVIEEL
LDEDQKVRPNEENNKDADLYTSRVMLSSQVPLEPPLLFLLEEYKNYLDAANMSMRVRRHSDPARRGELSV
CDSISEWVTAADKKTAVDMSGGTVTVLEKVPVSKGQLKQYFYETKCNPMGYTKEGCRGIDKRHWNSQCRT
TQSYVRALTMDSKKRIGWRFIRIDTSCVCTLTIKRGR

FIG. 6

Coding sequence of Mus musculus BDNF (SEQ ID NO: 3, Accession number BC034862)

>gi|22028400|gb|BC034862.1| Mus musculus brain derived neurotrophic
factor, mRNA (cDNA clone MGC:41191 IMAGE:1397218), complete cds
CCTGAGTTCCACCAGGTGAGAAGAGTGATGACCATCCTTTCCTTACTATGGTTATTTCATACTTCGGTT
GCATGAAGGCGCGGCCCATGAAAGAAGTAAACGTCCACGGACAACTTGGCCTACCCAGGTGTGCG
GACCCATGGGACTCTGGAGAGCGTGAATGGGCCCAGGCAGGTTCGAGAGGTCTGAGAGACATCACTG
GCTGACACTTTTGAGCACGTCATCGAAGAGCTTCCCGGGTTGGATGCTCAGCAGTCAAGTGCCTTTGGAGCCTCT
ACCATAAGGACGCGGACTTGTACACAAAATTACCTGAGCTTTGTGACAGTATTAGCGGTCACCCAG
ACTCTTTCTGCTGCCCCGCGTGGAATACATGTCTGCGGAGCTTGCCCTGAGTGCCTGTGTCCAGTCAAAATGTCTAGA
TCCGACCCTGCAGTGGACACTGGAACATCATTGGCTGACACTTTCGGGCCTACACTGACCATATGAATGGGCCGCCTA
AAAAGACTGCAGTAAACTCGGACCAATGCGAATCATGACGAGATAAGAGATTATAATTTATGAACCTGAAAGAAAAT
ACTGAAGACAGTATTCTACGAGACCAAGTGCCAATGCTACGGAGCTTACACCAGTCAATCGTATGTGTATATATATATAAAGGGG
AAAGAGAATTGGCTGGCATTCATAAGATAGATAATTATTTATGAACCTGAAAGAAAACAGTCATTTGCGCAAAACTTTAAA
AGATAGTGGATTTATGTTGTATAGAAAAAAAATTTTATGAACCTGAAAGAAAAACAGTCATTTGCGCAAAACTTTAAA
GTAAATTATTCAGTTAAGAACATTTATTGGACATATCCATGACCATGAAAGGAGAACAGTCATTAAACAAAAGTTTAA
GTTCTACAATCATTCCTCGATAATGTGCTCTTAATTGTGAATTGATAATAAACTGTCCCTCTTTCAGAAAAC
AAAAAATAATAATAAAAAAAAAAAAAAAAAAAAAAAAAAA
AGATTAAAAACAAAAAAAAAAAAAAAAAAAAAAA Polypeptide sequence of Mus musculus BDNF (SEQ ID NO: 4, Accession number AAH34862)

>gi|22028401|gb|AAH34862.1| Brain derived neurotrophic factor [Mus musculus]
MTILFLTMVISYFGCMKAAPMKEVNVHGQGNLAYPGVRTHGTLESVNGPRAGSRGLTTTSLADTFEHVIE
ELLDEDQKVRPNEENHKDADLYTSRVMLSSQVPLEPPLLFLLEEYKNYLDAANMSMRVRRHSDPARRGEL
SVCDSISEWVTAADKKTAVDMSGGTVTVLEKVPVSKGQLKQYFYETKCNPMGYTKEGCRGIDKRHWNSQC
RTTQSYVRALTMDSKKRIGWRFIRIDTSCVCTLTIKRGR

FIG. 7

Coding sequence for Rattus norvegicus BDNF (SEQ ID NO: 5, Accession number AY176065)

>gi|27652603|gb|AY176065.1| Rattus norvegicus brain-derived neurotrophic factor (Bdnf) mRNA, complete cds
ATGACCATCCTTTTCCTTACTATGGTTATTTCATACTTCGGTTGCATGAAGGCTGCGCCCATGAAAGAAG
CAAACGTCCACGGACAAGGCAACTTGGCCTACCCAGCTGTGCGGACACTTCTGGAGAGCGTGAA
TGGGCCCAGGCAGGTTCGAGAGCCAGTCTGGACACTTTGAGCACGTGATCGAA
GAGCTGCTGGATGATGCTGCAGCAAACATGAGCCGTGCTGCTGGAGGAATACAAAAA
CCCGGGGTGATGCTGCAGCAAACATGAGTCTATGAGTGGGTCCGCAGTCCCCGCCCAGTGCG
TTACCTGGTGTGACAGTAGTTAGGAAGTCTCAAAAGGTCCCTGTATCAAAAGACAACTGTCGGGCGC
AGCCGTGTGCACAGTCCCTTGGGTTACACAAAGAACTGAAGAAAGGCCCAGGAGACCAA
GGACCGGTCAATCCCAGTCGTACGTGCGGGCCCTTACCATGGATAGCAAAAGAGAATTGGCTGGCGATTCATAA
GTGCAACTACCCAGTCTTCTTGTGTATGTACCATTGACCATTAAAAGGGAAGATAG Polypeptide sequence of Rattus norvegicus BDNF (SEQ ID NO: 6, Accession number AA017828)

>gi|27652604|gb|AA017828.1| brain-derived neurotrophic factor [Rattus norvegicus]
MTILFLTMVISYFGCMKAAPMKEANVHGQGNLAYPAVRTHGTLESVNGPRAGSRGLTTSLADTFEHVIE
ELLDEDQKVRPNEENHKDADLYTSRVMLSSQVPLEPPLFLEEYKNYLDAANMSMRVRRHSDPARRGEL
SVCDSISEWVTAADKKTAVDMSGGTVTVLEKVPVSKGQLKQYFYETKCNPMGYTKEGCRGIDKRHWNSQC
RTTQSYVRALTMDSKKRIGWRFIRIDTSCVCTLTIKRGR

FIG. 8

MODULATION OF NEUROGLIA-DERIVED BDNF IN THE TREATMENT AND PREVENTION OF PAIN

CROSS REFERENCE TO RELATED APPLICATION APPLICATIONS

This application is the 371 National Phase of International Application No. PCT/CA2005/001501, filed Sep. 30, 2005, which was published in English under PCT Article 21(2) as International Publication No. WO 2006/042396. This application further claims the benefit, under 35 U.S.C. §119(e), of U.S. provisional application No. 60/620,722 filed Oct. 22, 2004. All of these applications are incorporated by reference in its their entirety.

FIELD OF THE INVENTION

The invention relates to the modulation of neuroglia-derived BDNF (brain-derived neurotrophic factor), and particularly relates to the modulation of neuroglia-derived BDNF for treating and preventing pain in a subject. The invention also relates to methods of identifying or characterizing compounds that may be used for the treatment or prevention of pain.

BACKGROUND OF THE INVENTION

The need for new and improved methods and agents for the treatment and prevention of pain is a significant ongoing concern in medicine. The therapeutics now being used mostly focus on the treatment of the symptoms of pain without treating the actual cause of pain. In addition, these therapeutics are not necessarily specific and can cause many undesirable side effects.

There remains a need to better define the mechanisms involved in pain sensation. There also remains a need to provide, based on the newly discovered mechanisms of nociception, new and specific therapeutics that can treat or prevent pain via intervention at the actual source of pain.

SUMMARY OF THE INVENTION

The invention relates to the modulation (e.g. decrease) of neuroglia-derived BDNF for the treatment or prevention of pain. The invention also relates to the identification or characterization of compounds capable of modulating (e.g. decreasing) neuroglia-derived BDNF.

In a first aspect, the present invention provides a method of treating or preventing pain in a subject, the method comprising decreasing neuroglia-derived BDNF in the subject.

In another aspect, the present invention provides a method for decreasing nociception in a subject, the method comprising decreasing neuroglia-derived BDNF in the subject.

In yet another aspect, the present invention provides a composition for the treatment or the prevention of pain in a subject, the composition comprising (a) an agent capable of decreasing neuroglia-derived BDNF in said subject; and (b) a pharmaceutically acceptable carrier.

In a further aspect, the present invention provides a package comprising the composition described herein together with instructions for its use for the treatment or prevention of pain. In still another aspect, the present invention provides a package comprising (a) an agent capable of decreasing neuroglia-derived BDNF in a subject; and (b) instructions for its use for the treatment or prevention of pain in said subject.

In still a further aspect, the present invention provides use of the composition described herein for the treatment or prevention of pain in a subject and/or for the preparation of a medicament for the treatment or prevention of pain. In yet a still further aspect, the present invention provides use of an agent capable of decreasing neuroglia-derived BDNF for the treatment or prevention of pain in a subject and/or use of an agent capable of decreasing neuroglia-derived BDNF for the preparation of a medicament for the treatment or prevention of pain in a subject.

In yet another embodiment, the present invention provides a method of identifying or characterizing a compound for the treatment or prevention of pain, the method comprising (a) contacting a test compound with a neuroglia expressing a BDNF or having a BDNF activity, and (b) determining whether the BDNF expression or activity is decreased in the presence of the test compound; wherein the decrease is an indication that the test compound may be used for treatment or prevention of pain.

In still another embodiment, the present invention provides a method of identifying or characterizing a compound for treatment or prevention of pain, the method comprising (a) contacting a test compound with a neuroglia comprising a first nucleic acid comprising a transcriptionally regulatory element normally associated with a BDNF gene, operably-linked to a second nucleic acid comprising a reporter gene capable of encoding a reporter protein, and (b) determining whether reporter gene expression or reporter protein activity is decreased in the presence of the test compound; wherein the decrease in reporter gene expression or reporter protein activity is an indication that the test compound may be used for treatment or prevention of pain.

In a further embodiment, the present invention provides a method of identifying or characterizing a compound for the treatment or prevention of pain, the method comprising (a) contacting a test compound with a neuroglia capable of secreting a BDNF polypeptide, and (b) determining whether the secretion of said BDNF polypeptide is decreased in the presence of the test compound; wherein a decrease in the secretion of the BDNF polypeptide is an indication that the test compound may be used for the treatment and prevention of pain.

In another embodiment, the present invention provides a method of identifying or characterizing a compound for the treatment or prevention of pain, the method comprising (a) contacting a test compound with neuroglia; and (b) determining whether the stimulation of said neuroglia is decreased in the presence of the test compound; wherein a decrease in the stimulation of said neuroglia is an indication that the test compound may be used for the treatment and prevention of pain.

In an embodiment, the present invention provides a method or an agent capable of decreasing a parameter selected from the group consisting of (a) BDNF expression in neuroglia, (b) BDNF release or secretion from neuroglia, (c) stimulation of neuroglia, (d) neuroglia-derived BDNF activity, and (e) any combination of (a) to (d).

In another embodiment, the neuroglia is selected from the group consisting of a microglia, an astrocyte and an oligodendrocyte, in a further embodiment, the neuroglia is located in the central nervous system of said subject. In another embodiment, the neuroglia is a stimulated neuroglia, in a further embodiment, the stimulated neuroglia has been contacted with ATP and/or the stimulated neuroglia is post-synaptic to a peripheral nerve or tract injury.

In still another embodiment, BDNF comprises an amino acid sequence substantially identical to a sequence selected from the group consisting of SEQ ID NOs: 2, 4, 6 and a fragment thereof.

In yet another embodiment, the signal of said pain originates in a peripheral nervous system (PNS) cell or in a central nervous system (CNS) cell. In embodiments, the pain is neuropathic pain, in a further embodiment, the neuropathic pain is associated with a nerve or tract injury and/or is selected from the group consisting of somatic and visceral pain. In yet another embodiment, the neuropathic pain is associated with a chemical insult. In a further embodiment, the pain is selected from the group consisting of chronic pain, chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, pain associated with drug intake and recurrent acute pain.

In still another embodiment, the method comprises administering to the subject an agent capable of decreasing neuroglia-derived BDNF in said subject. In another embodiment, the use, composition and package comprise such agents. In an embodiment, the agent is capable of decreasing or inhibiting the stimulation of neuroglia, in a further embodiment, the agent is an inhibitor of an ATP receptor, in a further embodiment, the ATP receptor is a P2X receptor, in a further embodiment, the agent is TNP-ATP. In another embodiment, the agent is capable of inhibiting BDNF expression, in a further embodiment, the agent is selected from the group consisting of an antisense molecule, a ribozyme, a siRNA and a siRNA-like molecule. In yet another embodiment, the agent is an antisense molecule, in a further embodiment, the antisense molecule is substantially complementary to a portion of a mRNA encoding a BDNF, in a further embodiment, the antisense molecule is complementary to a portion of a nucleic acid sequence substantially identical to a sequence selected from the group consisting of SEQ ID NOs: 1, 3 and 5. In yet another embodiment, the agent is a siRNA, in a further embodiment, the sequence of the siRNA is substantially identical to a sequence selected from the group consisting of SEQ ID NOs: 7, 8, 9, 10 and a fragment thereof. In yet another embodiment, the agent is administered intrathecally or is adapted for intrathecal administration.

In an embodiment, the subject is a mammal, in a further embodiment, the mammal is a human.

BRIEF DESCRIPTION OF THE DRAWINGS

FIG. 6. Coding (SEQ ID NO: 1, Accession number M37762) and polypeptide (SEQ ID NO: 2, Accession number AAA51820) sequences of human BDNF.

FIG. 7. Coding (SEQ ID NO: 3, Accession number BC034862) and polypeptide (SEQ ID NO: 4, Accession number AAH34862) sequences of mouse BDNF.

FIG. 8. Coding (SEQ ID NO: 5, Accession number AY176065) and polypeptide (SEQ ID NO: 6, Accession number AA017828) sequences of rat BDNF.

DETAILED DESCRIPTION OF THE INVENTION

Figure 1A:
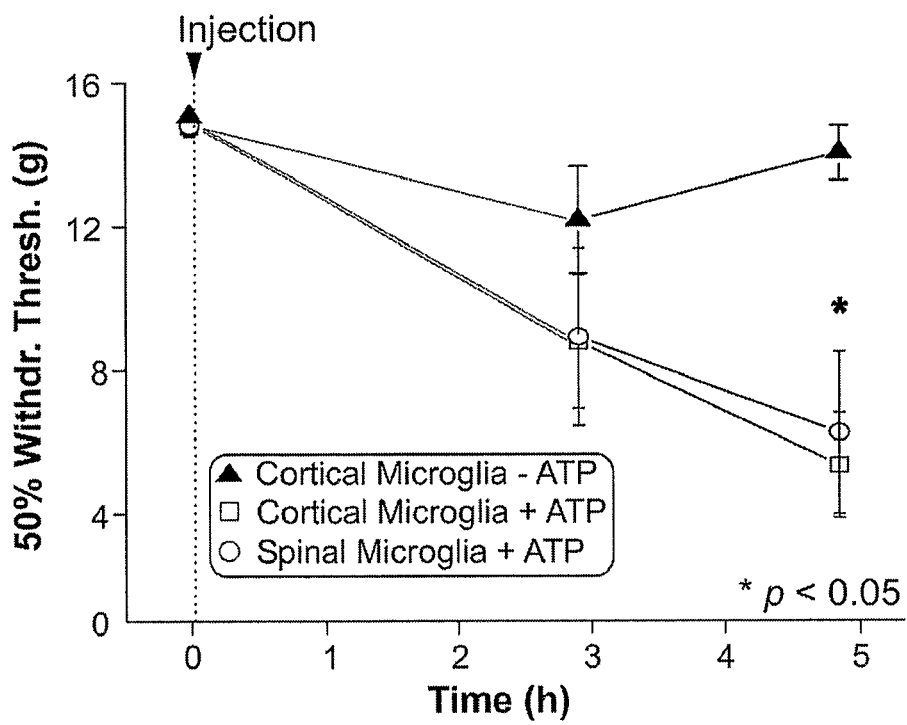
FIG. 1. Spinal delivery of ATP-stimulated microglia to rats via intrathecal catheter-evoked allodynia and a depolarizing shift in the transmembrane anion gradient of spinal lamina I neurons. A, In naïve rats, local spinal delivery of ATP-stimulated microglia (of cortical or spinal origin), but not resting microglia, caused a significant decrease in the mean paw withdrawal threshold ($WD_{50}$). B, left, Comparison of the mean $E_{anion}$ recorded in LI neurons from resting microglia- and ATP-stimulated microglia-injected rats (note that there were no significant changes in resting membrane potential of the cells). Right, Mean peak current evoked by GABA, measured in LI neurons at various values of Vm in slices taken from rats treated with ATP-stimulated or resting microglia in A. Horizontal standard error bars represent inter-neuron differences. Inset—Representative raw traces. C, Representative traces, in current clamp recording mode, showing that, at resting membrane potential, the postsynaptic response to GABA was depolarizing in a LI neuron taken from a rat with $WD_{50}$=3.4 g, in contrast to the response in a LI neuron taken from a rat with $WD_{50}$=12.6 g, where GABA was hyperpolarizing.

In a first aspect, the invention relates to methods and compounds for treating and preventing of pain, based on the modulation (e.g. decrease) of neuroglia-derived BDNF. As used herein, "BDNF" or "brain-derived neurotrophic factor" are used herein interchangeably and relate to a neurotrophic factor implicated in various neuronal processes, such as neurogenesis, synaptogenesis, repair of damaged networks, survival and differentiation of developing neurons, maintenance of mature neurons, normal synapses (e.g. inhibitory and/or excitatory) in the brain[14] and the spinal cord[15], modulation of dendritic and axonal growth and behavioral processes (e.g. antidepressant, mood stabilizing, memory). The BDNF polypeptide is ubiquitous in the central nervous system and is produced by various cellular sources, such as neurons (e.g. primary sensory neurons and postsynaptic neurons), neuroglia (e.g. microglia, astrocyte or oligodendrocyte) non-neural immune cells (e.g. lymphocyte (e.g. T and B lymphocyte), leulocyte, macrophage and endothelial cells. In embodiments, the BDNF polypeptide is produced and secreted by neuroglia (e.g. stimulated neuroglia). In embodiments, BDNF comprises the sequence of the polypeptide of SEQ ID NOs: 2 (human BDNF; see also FIG. 6), 4 (mouse BDNF; see also FIG. 7) or 6 (rat BDNF; see also FIG. 8), fragments thereof or sequences substantially identical thereto. In further embodiments, BDNF is encoded by the nucleic acid sequences capable of encoding the polypeptides of SEQ ID NOs: 2, 4 or 6, or fragments thereof or sequences substantially identical thereto or related by hybridization criteria (see below). In further embodiments, such nucleic acid sequences may comprise the sequence of SEQ ID NOs: 1 (human BDNF DNA; see also FIG. 6), 3 (mouse BDNF DNA; see also FIG. 7) or 5 (rat BDNF DNA; see also FIG. 18), fragments thereof or sequences substantially identical thereto or related by hybridization criteria (see below).

The invention also provides methods for decreasing neuroglia-derived BDNF by decreasing (1) BDNF expression in neuroglia; (2) BDNF release or secretion from neuroglia; (3) stimulation of neuroglia and/or (4) neuroglia-derived BDNF activity.

Therefore, in an embodiment, the present invention relates to methods for treating pain by decreasing neuroglia-derived BDNF. As used herein, a "neuroglia" is defined as a non-neuronal cell of the nervous system. In an embodiment, the neuroglia is located in the nervous system, and, in a further embodiment, in the central nervous system (e.g. the spinal cord). In an embodiment, the neuroglia is selected from a microglia, an astrocyte and a oligodendrocyte. In an embodiment, the neuroglia is an oligodendrocyte. Oligodendrocytes typically form the myelination of the white matter and surround cell bodies in the gray matter. They are large, with few ramifications wrapping around neurons. In another embodiment, the neuroglia is an astrocyte. Astrocytes typically form the link between blood vessels and neurons. They are smaller than oligodendrocytes and possess extensive ramifications. In another embodiment, the neuroglia is a microglia. Microglia play an immune function in the nervous system. Once activated or stimulated, the microglia may phagocytose debris. They are very small cells but become enlarged once they are activated or stimulated. In embodiments, neuroglia usually express OX-42 (CR3/CD11b), glial fibrillary acidic protein and/or RIP. As used herein, the term "neuroglia-derived BDNF" is defined as BDNF produced, released or secreted by a neuroglia, and in embodiments, includes BDNF produced or secreted by a microglia, astrocyte and/or an oligodendrocyte.

In a further embodiment, modulators (e.g. inhibitors) of BDNF activity or expression can be used to treat or prevent pain or to decrease nociception in a subject. In an embodiment, the inhibitors (e.g. agents or compounds) may be administered intrathecally. In an embodiment, these modulators are agents capable of decreasing BDNF downstream signaling (such as inhibitors of the BDNF receptor (e.g. TrkB or $p75^{NTR}$), e.g. K-252a or an anti-TrkB antibody; inhibitors of the MAPK (ras mitogen-activated protein kinase) pathway; inhibitors of the $PI_3K$-Akt (phosphatidylinositol-3 kinase-Akt) pathway; inhibitors of the PLCγ (phospholipase Cγ) pathway). In another embodiment, these modulators are compounds capable of inhibiting stimulation (e.g. ATP stimulation) of neuroglia (such as inhibitors of the P2X (e.g. $P2X_4$ and $P2X_7$) receptor, e.g. TNP-ATP, minocycline and propentophylline). In yet another embodiment, these modulators are compounds or agents capable of decreasing BDNF expression (such as dsRNA BDNF, siRNA molecule, siRNA-like molecule, anti-sense oligonucleotide, ribozyme, etc.). In an embodiment, when the agent or compound is an antisense oligonucleotide, it is substantially complementary to a portion of an mRNA encoding a BDNF, and in a further embodiment, it is complementary to a portion of a nucleic acid sequence substantially identical to a sequence selected from the group consisting of SEQ ID NO: 1, 3 and 5. In yet a further embodiment, when the agent or compound is a siRNA, the sequence of the siRNA is substantially identical to a sequence selected from the group consisting of SEQ ID NO: 7, 8, 9, 10 and a fragment thereof.

In an embodiment, the invention also relates to the treatment of acute and chronic pain, more specifically to the treatment of neuropathic pain. "Neuropathic pain", as used herein, refers to chronic pain associated with nerve injury (e.g. following a chemical insult, following crush or transection, following compression of nerves, following nerve degeneration resulting from disease, following chemical insult) in the central nervous system. In an embodiment, the chemical insult may result from chemotherapy. In an embodiment, neuropathic pain is associated with a nerve or tract injury. In a further embodiment, the neuropathic pain is associated with visceral and/or somatic pain. In embodiments, the signal of pain may originate in a peripheral nervous system cell or a sensory fiber transsynaptic to the neuroglia. In embodiments, the pain may be associated with many conditions such as chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, pain associated with drug intake and/or recurrent acute pain. In an embodiment, the pain associated with drug intake is a pain associated with chemotherapy treatment.

The methods described herein also relate to decreasing neuroglia-derived BDNF to reduce nociception. "Nociception" as used herein refers to the sensory component of pain. Pain may be the result of various stimuli, including but not limited to pressure, injury, thermal stimuli or chemical (e.g. ionic) stimuli.

"BDNF activity" as used herein refers to any detectable phenotype associated with BDNF. For example, BDNF activity can be assessed by measuring the level of TrkB tyrosine phosphorylation (e.g. using Western blotting), the level of MAPK (ERK) pathway activation (e.g. using Western blotting), the level of Akt phosphorylation (e.g. using Western blotting), the level of PLCγ pathway activation, the level of reports of neurotransmitter release, the level of NMDA receptor phosphorylation, cell survival, cell differentiation and cell death (e.g. apoptosis). A number of assays for apoptosis may be used, such as TUNEL staining, Annexin V staining, FACS analysis, agarose electrophoresis, Western blot, histology, electron microscopy, caspase assay, ELISA, mitochondrial assay (e.g. cytochrome C release assay), cathepsin and calpain assays, etc. In embodiments, BDNF activity may also affect the neural cell's (e.g. LI neuron) anion reversal potential ($E_{anion}$). The anion reversal potential may be determined, for example, by using gramicidin-perforated patch clamp recording (see below in the Examples section).

"BDNF expression" relates both to production of a BDNF transcript and/or the secretion a BDNF polypeptide or protein. BDNF expression may therefore, in embodiments, be determined by assessing protein levels directly (e.g., by immunocytochemistry, ELISA and/or western analysis) or a level of a BDNF-encoding nucleic acid (e.g. BDNF mRNA levels or transcripts). These levels may be determined by using, for example, methods such as reverse-transcriptase polymerase chain reaction [RT-PCR] methods, micro-array-based methods or by Northern analysis.

Compounds capable of decreasing BDNF activity or expression in a neuroglia may, for example, be administered in a way such that they contact a CNS tissue or a CNS cell. The compounds that can be used include, but are not limited to, those which directly or indirectly modify the activity of the protein and those which modulate the production and/or stability of the protein (e.g. at the level of transcription, translation, maturation, post-translational modification, phosphorylation, secretion and degradation).

One class of such compounds are those that act via the inhibition of stimulation of neuroglia. In fact, BDNF is secreted in response to the stimulation (e.g. ATP stimulation) of neuroglia. Many compounds are known in the art to inhibit activation of microglia. By inhibiting activation of neuroglia, these compounds limit the secretion of BDNF and thereby can be used for the prevention or treatment of pain. These compounds include, but are not limited P2X receptor (e.g. $P2X_4$ and $P2X_7$) inhibitors such as TNP-ATP.

Another class of compounds that can be used to limit BDNF's expression are compounds that lower the level of BDNF transcripts. By doing so, these compounds limit the number of BDNF polypeptides that can be produced and can therefore be use to treat or prevent pain. These compounds include, but are not limited to, a dsRNA (e.g. SEQ ID NO: 7, 8, 9 or 10), siRNA, siRNA-like molecule, antisense oligonucleotide or ribozyme.

A further class of compounds or agents that can be used to treat or prevent pain are compounds capable of inhibiting the mediation of a BDNF signal. These compounds can act, for example, on the BDNF receptor such as TrkB or $p75^{NTR}$. In an embodiment, the BDNF receptor is the TrkB receptor. Compounds that may inhibit TrkB signaling include, but are not limited to, K-252a (commercially available from Calbiochem) or a neutralizing antibody against TrkB (anti-TrkB antibody [e.g. IgG]) (commercially available from BD Transduction Laboratories). Alternatively, these compounds can act on the various signaling pathways that are activated upon the ligation of BDNF with its receptor.

Further, modulation of BDNF expression may also arise from modulation (e.g. mediated by phosphorylation) of transcription factors which regulate BDNF expression. Such transcription factors include, but are not limited to, NFκB and Brn-3c.

In addition, modulation of BDNF activity may also be achieved by modulating (e.g. decreasing) BDNF secretion from neuroglia.

The methods described herein also contemplate modulating (e.g. enhancing) BDNF degradation. Such enhanced degradation may take place intracellularly in the cell producing BDNF (e.g. neuroglia) or in the cell harboring the BDNF receptor (e.g. neuronal cell having a BDNF receptor such as TrkB or $p75^{NTR}$). In the latter case, prior to its degradation, BDNF has been transferred intracellularly following contacting the BDNF receptor. In another embodiment, the augmented rate of degradation can also be observed extracellularly, once BDNF has been secreted.

In an embodiment, the methods and uses described herein apply to a vertebrate subject. In another embodiment, the subject is a mammal, in a yet further embodiment, a human.

As noted above, a homolog, variant and/or fragment of a BDNF which retains activity may also be inhibited in the methods described. Homologs include protein sequences which are substantially identical to the amino acid sequence of a BDNF, sharing significant structural and functional homology with a BDNF. Variants include, but are not limited to, proteins or peptides which differ from a BDNF by any modifications, and/or amino acid substitutions, deletions or additions. Modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of a BDNF or a fragment or a portion of a homolog or variant of a BDNF.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a given sequence (nucleic acid or amino acid) is "homologous" to another sequence if the two sequences are substantially identical and the functional activity of the sequences is conserved (as used herein, the term "homologous" does not infer evolutionary relatedness). Two nucleic acid sequences or two amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs: 1 to 10.

Substantially complementary nucleic acids are nucleic acids in which the "complement" of one molecule is substantially identical to the other molecule.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

The invention further provides a composition for the prevention and/or treatment of pain comprising an agent capable of decreasing neuroglia-derived BDNF in admixture with a pharmaceutically acceptable carrier. In embodiments, the agent is capable of decreasing (1) BDNF expression in neuroglia; (2) BDNF release or secretion from neuroglia; (3) stimulation of neuroglia; and/or (4) neuroglia-derived BDNF activity. In an embodiment, such a composition is suitable for or adapted for administration to a CNS neural cell or tissue, such as spinal cord tissue or cell. In yet a further embodiment, such a composition may be an inhibitor of BDNF expression or activity. As used herein, an "inhibitor" is a compound that downregulates or decreases directly or indirectly the expression of the BDNF gene, stability of the BDNF mRNA or transcript, translation of the BDNF mRNA or transcript, maturation of the BDNF polypeptide, transport, and/or the secretion of the BDNF polypeptide. In an embodiment, the "inhibitor" can also down-regulate or inhibit BDNF activators (such as transcription factors enhancing BDNF's gene expression (e.g., NFκB and Brn-3c)). In embodiments, the BDNF may be derived a from microglia, astrocyte and/or an oligodendrocyte. In a further embodiment, the composition may be adapted for intrathecal administration.

The invention further provides use of the above-mentioned composition or the above-mentioned agent or compound, capable of decreasing neuroglia-derived BDNF for the treatment or prevention of pain. The invention also provides use of the above-mentioned composition or the above-mentioned agent, capable of decreasing BDNF activity or expression for the preparation of a medicament for treatment or prevention of pain. In another embodiment, the agent may be formulated for administration to a CNS tissue, e.g. CNS cell, of a subject. In yet another embodiment, the agent may be adapted for intrathecal administration. In a further embodiment, the compound may be, for example, an inhibitor of BDNF expression or activity.

The invention further provides kits or packages (e.g. commercial packages) comprising the above-mentioned compositions or agents together with instructions for their use for the treatment or prevention of pain.

In various embodiments, an agent capable of modulating, e.g. decreasing, neuroglia-derived BDNF may be used therapeutically in formulations or medicaments to treat pain. The invention also provides corresponding methods of medical treatment, in which a therapeutic dose of an agent capable of modulating, in an embodiment decreasing, neuroglia-derived BDNF, is administered in a pharmacologically acceptable formulation. Accordingly, the invention also provides therapeutic compositions comprising a compound capable of modulating, in an embodiment, decreasing BDNF activity or expression, and a pharmacologically acceptable excipient or carrier. The therapeutic composition may be soluble in an aqueous solution at a physiologically acceptable pH.

In an embodiment, the agent described herein may be administered such that it comes into contact with a CNS tissue or a CNS neuron. As used herein, the "central nervous system" or CNS is the portion of the nervous system comprising the brain and the spinal cord (e.g. in the lumbar region). By contrast, the "peripheral nervous system" or PNS is the portion of the nervous system other than the brain and the spinal cord. In an embodiment, the CNS tissue is the superficial dorsal horn, in a further embodiment, a lamina I neuron. As such, in embodiments, an agent of the invention can be administered to treat CNS cells in vivo via direct intracranial or intrathecal injection or injection into the cerebrospinal fluid. Alternatively, the agent can be administered systemically (e.g. intravenously, or orally) in a form capable of crossing the blood brain barrier and entering the CNS. "Neural" and "neuronal" are used herein interchangeably and both relate to neurons. "Non-neuronal" is used herein to relate to cells other than neurons, and in the context of cells of the nervous system, relates to cells of the nervous system other than neurons (e.g. neuroglia).

The invention also provides pharmaceutical compositions (medicaments) comprising an agent capable of modulating, e.g. decreasing neuroglia-derived BDNF in a CNS cell. In an embodiment, such compositions include the agent, in a therapeutically or prophylactically effective amount sufficient to treat or attenuate pain, and a pharmaceutically acceptable carrier. A "therapeutically effective amount" refers to an amount effective, at dosages and for periods of time necessary, to achieve the desired therapeutic result, such as reduction of pain. A therapeutically effective amount of an agent capable of modulating, in an embodiment decreasing, neuroglia-derived BDNF, may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting onset of pain or increases in the severity of pain. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, intracranial, intrathecal, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compound capable of modulating, in an embodiment decreasing or downregulating, neuroglia-derived BDNF, can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a compound capable of decreasing neuroglia-derived BDNF) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a compound capable of modulating, in an embodiment decreasing, neuroglia-derived BDNF, may be formulated with one or more additional compounds that enhance its solubility.

In accordance with another aspect of the invention, therapeutic compositions of the present invention, comprising an agent capable of decreasing neuroglia-derived BDNF, may be provided in containers or packages (e.g. commercial packages) which further comprise instructions for their use for the treatment or prevention of pain.

Given that a decreased in neuroglia-derived BDNF correlates with a decrease in pain sensation as described herein, a further aspect of the present invention is the treatment of pain by administering to a subject a nucleic acid molecule encoding a BDNF inhibitor, such as a dsRNA, siRNA, antisense oligonucleotide or ribozyme. Suitable methods of administration include gene therapy methods (see below).

A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263: 14621; Wilson et al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126).

Defective retroviruses are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .psi.Crip, .psi.Cre, .psi.2 and .psi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a nucleic acid compound of the invention, but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Lentiviral gene therapy vectors may also be adapted for use in the invention.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, Science 288:627-9 (2000); and Cavazzana-Calvo et al., Science 288:669-72 (2000)).

Given the correlation between neuroglia-derived BDNF and pain, compounds which are capable of decreasing, such neuroglia-derived BDNF can be used for the prevention and treatment of pain. Therefore, the invention further relates to screening methods for the identification and characterization of compounds capable of decreasing neuroglia-derived BDNF.

Therefore, the invention further provides a method of determining whether a candidate or test compound is capable of decreasing neuroglia-derived BDNF activity or expression, and in turn is useful for the prevention and treatment of pain. Such a method may comprise assaying BDNF activity and/or expression in a suitable system in the presence versus the absence of a candidate compound. In an embodiment, the method comprises contacting a neuroglia having a BDNF activity or expressing a BDNF with said candidate compound and determining whether the BDNF activity or expression has decreased in the presence of the test compound. A decrease in BDNF activity or expression is indicative that the test compound may be used for the treatment or the prevention of pain. In an embodiment, the neuroglia is a stimulated neuroglia (e.g. ATP-stimulated neuroglia or post-synaptic to a peripheral nerve or tract injury). In another embodiment, the neuroglia is selected from a microglia, an astrocyte and an oligodendrocyte. In yet a further embodiment, the neuroglia endogenously expresses BDNF. In an another embodiment the above-mentioned neuroglia has been genetically engineered to express a BDNF gene. The methods described herein can be used to screen for test compound such as dsRNA, siRNA molecule, siRNA-like molecule, ribozyme and/or antisense oligonucleotide.

The invention also provides another screening method to identify or characterize compounds that can be used in the treatment or prevention of pain. In an embodiment, the method comprises contacting a neuroglia cell with a candidate compound and determining whether the neuroglia stimulation has decreased in the presence of the test compound. A decrease in neuroglia activation is indicative that the test/candidate compound may be used for the treatment or the prevention of pain. In an embodiment, the neuroglia is a stimulated neuroglia (e.g. ATP-stimulated neuroglia or post-synaptic to a peripheral nerve or tract injury). In another embodiment, the neuroglia is selected from a microglia, an astrocyte and an oligodendrocyte.

As noted above, the invention further relates to methods for the identification and characterization of compounds capable of decreasing BDNF gene expression. Such a method may comprise assaying BDNF gene expression in the presence versus the absence of a test compound. Such gene expression may be measured by detection of the corresponding RNA or protein, or via the use of a suitable reporter construct comprising a transcriptional regulatory element(s) normally associated with a BDNF gene, operably-linked to a reporter gene. A first nucleic acid sequence may "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, and/or green fluorescent protein.

In an embodiment, a candidate compound may further be assayed to determine if it is capable of modulating a BDNF-mediated process or BDNF activity.

The invention also provides a further screening method for compounds that can be used in the treatment or prevention of pain based on their ability to decrease the ability of a neuroglia to secrete BDNF. In an embodiment, the method comprises contacting the test compound in the presence of a cell capable of secreting BDNF (such as a neuroglia) and determining whether the secretion of BDNF is decreased in the presence of the test compound. The decrease in BDNF secretion from neuroglia is an indication that the test compound may be used in the treatment or prevention of pain. In an embodiment, the neuroglia is a stimulated neuroglia (e.g. ATP-stimulated neuroglia or post-synaptic to a peripheral nerve or tract injury). In an embodiment, the neuroglia is selected from a microglia, an astrocyte and an oligodendrocyte.

The screening methods mentioned herein may be employed either with a single test compound or a plurality or library (e.g. a combinatorial library) of test compounds. In the latter case, synergistic effects provided by combinations of compounds may also be identified and characterized. The above-mentioned compounds may be used for prevention and/or treatment of pain, or may be used as lead compounds for the development and testing of additional compounds having improved specificity, efficacy and/or pharmacological (e.g. pharmacokinetic) properties. In an embodiment the compound may be a prodrug which is altered into its active form at the appropriate site of action, e.g. in CNS tissue (e.g. in the spinal cord). In certain embodiments, one or a plurality of the steps of the screening/testing methods of the invention may be automated.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Materials and Methods

Peripheral Nerve Injury Model and Behavioural Studies.

Figure 5A:
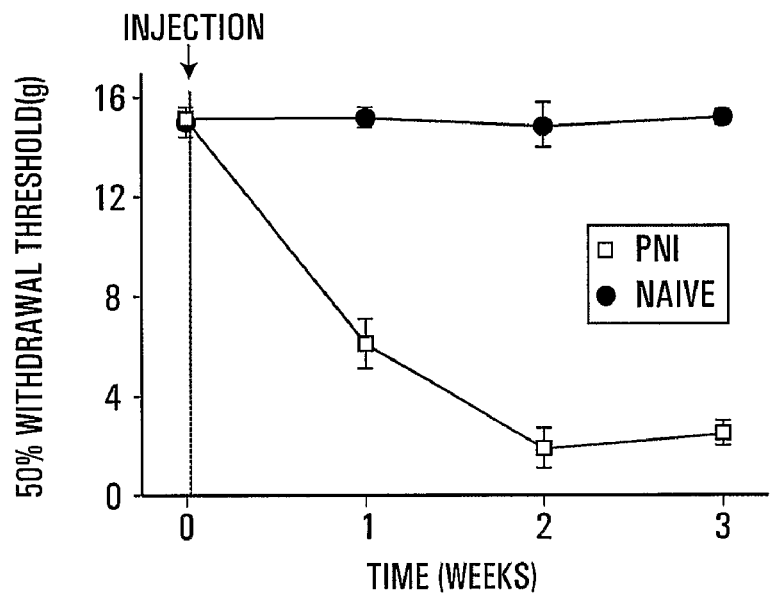
FIG. 5. A, Following PNI, but not sham surgery, the nociceptive withdrawal threshold ($WD_{50}$) to mechanical stimulation of adult rats dropped significantly over the course of 2-3 weeks. B & C, Micrographs illustrating that OX-42 staining (indicative of activated microglia) is much more intense in the ipsilateral dorsal horn of PNI rats (right) compared to sham-operated rats (left). Scale bar in C is 0.2 mm; SDH ipsi.=superficial dorsal horn ipsilateral to PNI. D, Pooled data showing that perfusion of TNP-ATP (1 µM) onto slices taken from rats that had received PNI elicited a significant hyperpolarization of $E_{anion}$ in LI neurons.
Figure 5B:
Figure 5C:
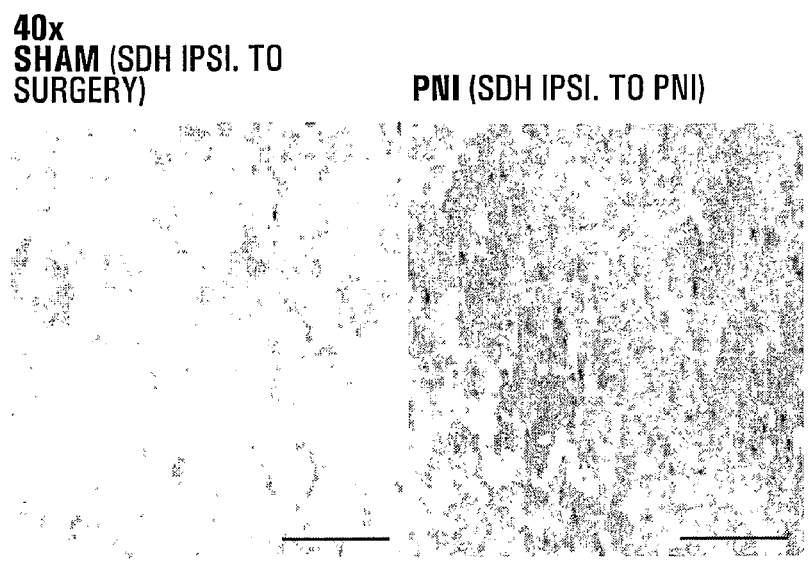
Figure 5D:
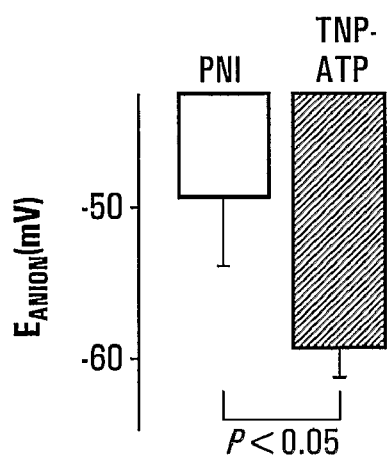

Peripheral nerve injury was induced by surgically implanting a polyethylene cuff (2 mm in length, inner diameter 0.7 mm) around the sciatic nerve of adult male Sprague-Dawley rats[3,17]. For sham surgery, which was used as a control, animals had all surgical procedures exempt that the cuff was not implanted. The 50% withdrawal threshold, or 50% paw withdrawal threshold, to mechanical stimulation was assessed[3,18]. Subsequent to nerve injury, only animals that showed a gradual decrease in mechanical threshold (over 14-17 days) down to 2 g or less were used for further experiments. In animals with peripheral nerve injury induced in this model, there was microglial activation in the spinal cord ipsilateral to the nerve cuff, as indicated by increased labeling for the microglial activation marker OX-42 (FIGS. 5B and 5C).

Slice preparation. Parasagittal slices (300-350 µm) of spinal cord were prepared from adult (>50 days old) male rats as previously described[31]. Slices were continually superfused (2-3 ml min$^{-1}$) with artificial cerebrospinal fluid (ACSF) containing (in mM): 126 NaCl, 26 NaHCO$_3$, 10 glucose, 2.5 KCl, 2 CaCl$_2$, 2 MgCl$_2$, 1.25 NaH$_2$PO$_4$ (bubbled with 95% O$_2$/5% CO$_2$, pH ~7.4).

Recordings. For perforated-patch recordings, the pipette tip was filled with a solution containing (in mM): 130 potassium methyl sulphate (KMeSO$_4$), 5 CsCl, 2 MgCl$_2$, 11 BAPTA, 1 CaCl$_2$, 4 ATP, 0.4 GTP, 10 HEPES (~pH 7.4). The pipette was back-filled with this same solution supplemented with 25 µg ml$^{-1}$ gramicidin D [gramicidin stock was at 10 mg ml$^{-1}$ in dimethylsulphoxide (DMSO)]. Recordings in this mode were selected when access resistance was stable between 25-45 MΩ. For whole-cell voltage-clamp recordings, pipettes were filled with the above solution lacking gramicidin D. GABA was applied locally for 10-50 ms by pressure ejection through a micro-pipette. Data acquisition and analysis of PSCs were performed as previously described[19]; membrane potential measurements were corrected as previously described[20]. Neither input resistance nor resting membrane potential of LI neurons was affected significantly by any of the drugs or protocols used in this study. All measurements are given as means±SEM, except where indicated. Statistical significance was tested using Student's t-tests for comparison of mean values, chi-squared tests for contingency tables, and mixed-design analyses of variance (post-hoc Tukey's HSD test) for repeated measures.

Microglial cultures. Rat primary cultured microglia were prepared under standard conditions as described[2,21]. In brief, mixed glial culture was prepared from neonatal Wistar rats and maintained for 10-16 days in DMEM medium with 10% fetal bovine serum. Microglia were separated from the primary culture by gentle shaking of the flask and replated on plastic dishes. The cells were removed from the dish surface using a cell scraper and collected in 100 µl of PBS; subsequently, the cell density of microglia was measured using a cell counter and the volume of PBS adjusted to give a final density of 1000 cells/10 µl. This method produces microglial cultures of >95% purity. For ATP-stimulation, the purified microglia were incubated with ATP (50 µM) for 1 hour.

Intrathecal injections and ELISA. At least three days before drug administration, rats were anaesthetized with sodium pentobarbital (65 mg kg$^{-1}$), and a lumbar spinal catheter (PE-10 polyethylene tube) was inserted into the intrathecal space[22]. On recovery from surgery, lower-body paralysis was induced through intrathecal lidocaine (2%, 30 µl) injection to confirm proper catheter localization. Only animals exhibiting appropriate, transient paralysis to lidocaine, as well as a lack of motor deficits, were used for behavioural testing. Following drug/vehicle administration, animals were killed and their vertebral column dissected to visually confirm correct placement of the catheter. Drugs included BDNF (10 µg/day or 10 µg/injection) and anti-TrkB antibody (12 µg every 2 hrs or 30 µg/injection), TrkB-Fc (5 µg/injection), all of which were prepared in saline+10% (v/v) DMSO. For viral-mediated transduction, adenoviral vectors encoding BDNF and EGFP[28] were administered once (20 µl; 2.0×10$^{10}$ PFU/ml). At the doses used, none of the compounds produced motor disturbances or sedation, as assessed by grasping, righting and placing reflexes and behavioural observations[23]. For experiments in which microglia were lipofected with small interfering RNA (siRNA), anti-BDNF and scrambled siRNA were obtained from Dharmacon Inc. The BDNF siRNA consisted of four pooled 21-nucleotide duplexes. The sequences of the four duplexes were as follows[6]:

```
1) TCGAAGAGCTGCTGGATGA      (SEQ ID NO: 7)

2) TATGTACACTGACCATTAA      (SEQ ID NO: 8)

3) GAGCGTGTGTGACAGTATT      (SEQ ID NO: 9)

4) GAACTACCCAATCGTATGT      (SEQ ID NO: 10)
```

Microglial cultures were transfected with BDNF or scrambled siRNA with Lipofectamine 2000™ following the manufacturer's instructions. Briefly, siRNA and lipofectamine were diluted in serum-free medium, mixed and added to the microglial cultures. Transfection was allowed to occur for 5 hours and the microglia collected as above for subsequent intrathecal injection. In all cases, 30 µl microglia+ supernatant were injected intrathecally in normal rats. Immunohistochemistry. Immunohistochemistry was performed on perfused, free-floating sections. OX-42 (Cedarlane, 1:1000) which labels CR3/CD11b was used as a specific marker for microglia. After overnight incubation at 4° C. with the primary antibody, sections were rinsed and incubated with biotinylated anti-mouse IgG (1:1000) for 1 h at room temperature. Sections were then rinsed again and immersed for 1 h in an avidin-biotinperoxydase complex (Vector Laboratories). Finally, positive labelling was visualized with 0.05% 3,3'-diaminobenzidine (DAB) containing 0.0039 hydrogen peroxide.

To measure BDNF secretion, microglia were prepared under the various experimental conditions described above and incubated at 37° C. for 6 hours to model the above in vivo experiments.

Calcium imaging. Spinal cord slices were prepared for calcium imaging and tested for responses to GABA as previously described[5]. Primary cultures of microglia were prepared as above, transferred to standard cover slips and incubated with 2.5 µM Fura-2-AM in HEPES-buffered saline (+0.01% DMSO) for 45 min. Following fluorophore loading, changes in $[Ca^{2+}]_i$ in individual microglia was evoked using brief (~5 s) applications of ATP (10 µM) from a micro-pipette. $[Ca^{2+}]_i$ was fluorometrically measured using a 40× water-immersion objective on a Zeiss Axioscope equipped with epifluorescence optics. Images were acquired using a TILL Photonics monochromator coupled to a CCD camera, and regions of interest (for ratioing) were drawn on clearly distinct neuronal cell bodies.

Example 2

Results

To investigate whether microglia may affect $E_{anion}$ in lamina I (LI) neurons, Applicant administered microglia via an intrathecal catheter to the lumbar spinal level of naïve rats in vivo, as previously described[2], and subsequently made perforated-patch and whole-cell recordings from LI neurons in vitro in acute spinal cord slices prepared from these animals. Before sacrificing each animal, Applicant determined the nociceptive withdrawal threshold to confirm the presence or not of tactile allodynia in response to the treatment[2,3]. In animals in which Applicant administered microglia that had been stimulated with ATP (50 µM), the nociceptive withdrawal threshold progressively decreased reaching a minimum after approximately 5 hours (FIG. 1A). By contrast, in animals treated with control, unstimulated, microglia there was no change in withdrawal threshold (FIG. 1A). Applicant found that cortically and spinally derived microglia produced a comparable decrease in paw withdrawal threshold. Because of the larger size of the cortex, it yielded more microglia and was therefore used for subsequent investigations.

Figure 1B:
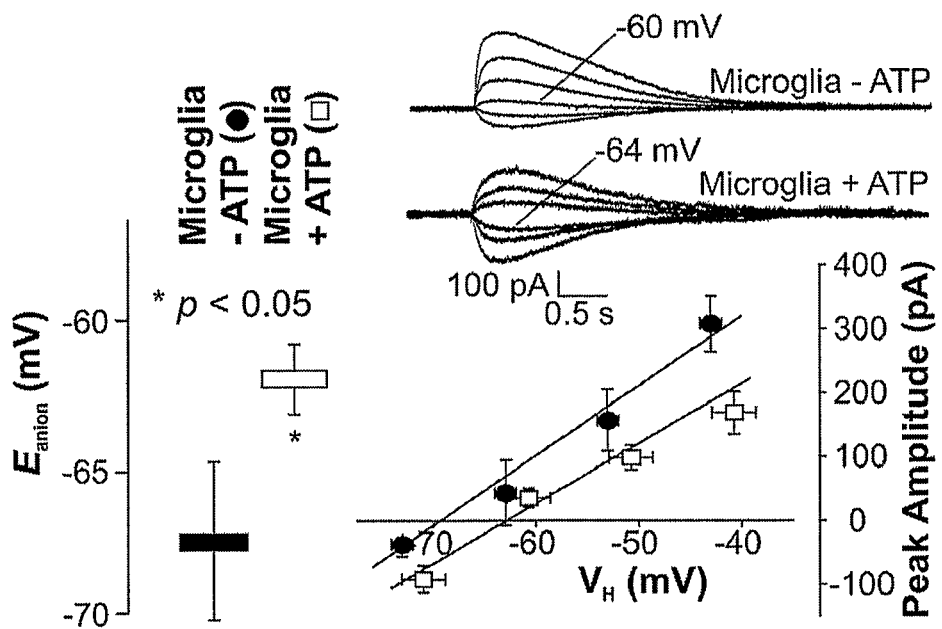
Figure 1C:
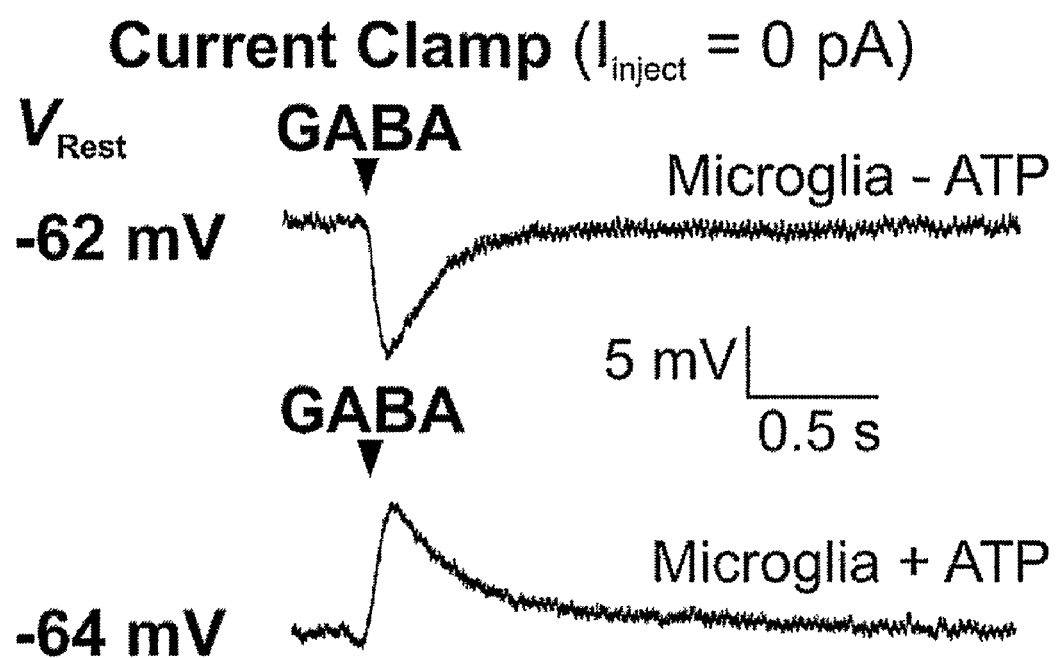

Electrophysiological recordings were made from slices prepared 5 hours after intrathecal microglia administration. Using voltage-clamp recording from LI neurons, Applicant found that in spinal slices taken from rats injected with control microglia, $E_{anion}$ was $-68.3 \pm 1.8$ mV (n=6; FIG. 1B). On the other hand, in LI neurons from rats following administration of ATP-stimulated microglia $E_{anion}$ was $-61.6 \pm 1.1$ mV (n=16, $p<0.0001$). Using current-clamp recordings, Applicant found that GABA caused hyperpolarization in the LI neurons from control animals (FIG. 1C upper) whereas GABA produced depolarization in the neurons from rats in which ATP-stimulated microglia had been administered (FIG. 1C, lower). Thus, intrathecal administration of ATP-stimulated microglia produced a depolarizing shift in $E_{anion}$ in LI neurons and converted GABA-evoked responses from hyperpolarizing to depolarizing. These changes in inhibitory responses coincided with the reduction in nociceptive withdrawal threshold produced by the ATP-stimulated microglia.

In order to effect the shift in $E_{anion}$, ATP-stimulated microglia may signal to the LI dorsal horn neurons. Activated microglia are known to secrete various biologically active signalling molecules, one of which is BDNF, which has been implicated in both the hypersensitivity of dorsal horn neurons that follows sensitization and inflammation[25,26] and in anion gradient shifts in the hippocampus[27]. Applicant administered BDNF intrathecally to naïve rats and found that it produced a decrease in paw withdrawal threshold comparable to that produced by the ATP-stimulated microglia (FIG. 2A).

Figure 2C:
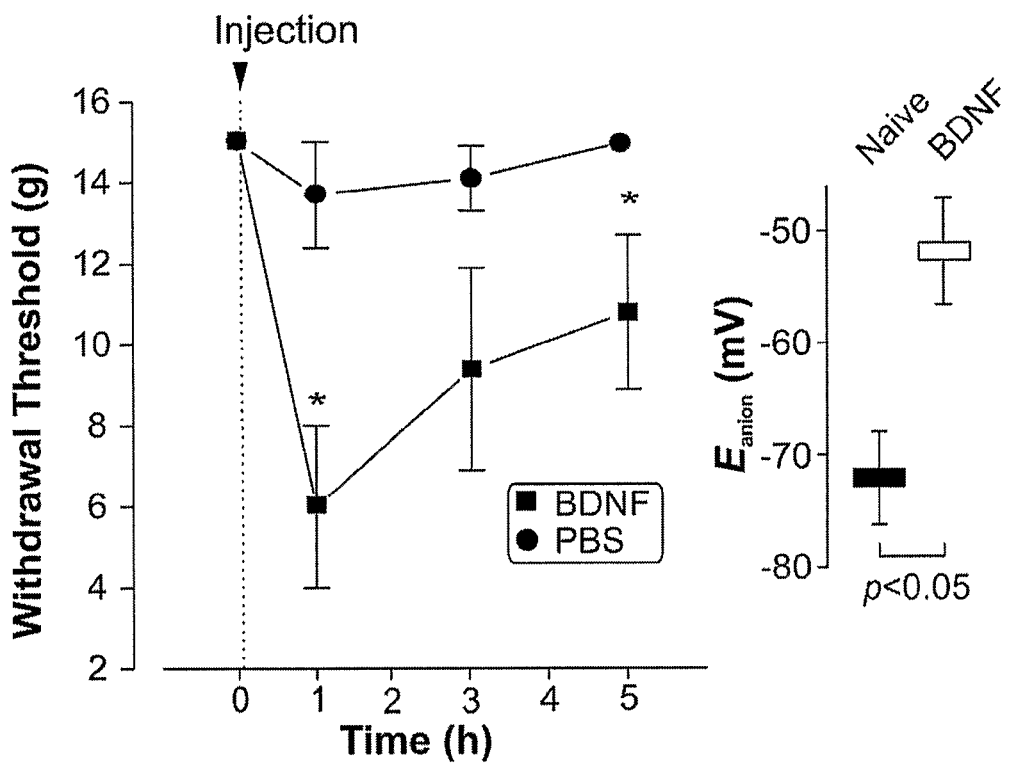
FIG. 2. Enhanced concentrations of BDNF in the dorsal horn elicited nociceptive hypersensitivity and a depolarizing shift in the transmembrane anion gradient of spinal lamina I neurons. A, Intrathecal delivery of recombinant human BDNF (20 μg) to the lumbar dorsal horn of intact rats led to a significant and transient decrease in the $WD_{50}$ within 1 hour, compared to saline control, which elicited no significant decrease. B, Significant depolarization of mean $E_{anion}$ in LI neurons in slices treated with BDNF (50 ng/ml; for >90 min) vs. slices in control ACSF (Naïve). C, Representative traces of calcium measurements from Fura-2-AM-loaded LI neurons showing that brief GABA application in slices superfused with BDNF could cause a bicuculline-sensitive increase in intracellular calcium ($[Ca^{2+}]_i$). The viability of cells not responding to GABA was confirmed via KCl-mediated responses. Bottom right inset, The proportion of LI neurons showing GABA-mediated rise in $[Ca^{2+}]_i$ increased progressively reaching 31% between 80-120 min of continuous BDNF perfusion ($\chi^2_{corrected}$=5.15). In contrast, only 2% of cells responded with a rise in $[Ca^{2+}]_i$ over a similar time period in absence of BDNF (C; $\chi^2_{corrected}$=6.74). D, Intrathecal administration of a BDNF transducing adenoviral vector (adBDNF)[11] triggered a delayed and progressive decrease in $WD_{50}$ that persisted as long at 4 days post-injection. In contrast, administration of control adenovirus, not encoding BDNF (adGFP) elicited no decrease in paw withdrawal threshold. E, Significant depolarization of mean $E_{anion}$ in LI neurons in slices taken from adBDNF- vs. adGFP-treated rats in D. F, Mean peak current evoked by GABA measured in LI neurons at various values of Vm in slices taken from rats treated with adBDNF or adGFP in D. Horizontal standard error bars represent interneuron differences. G, Representative trace, in current clamp recording mode, showing that brief GABA application to a LI neuron in a slice taken from an adBDNF-treated rat could elicit action potentials.
Figure 2C:
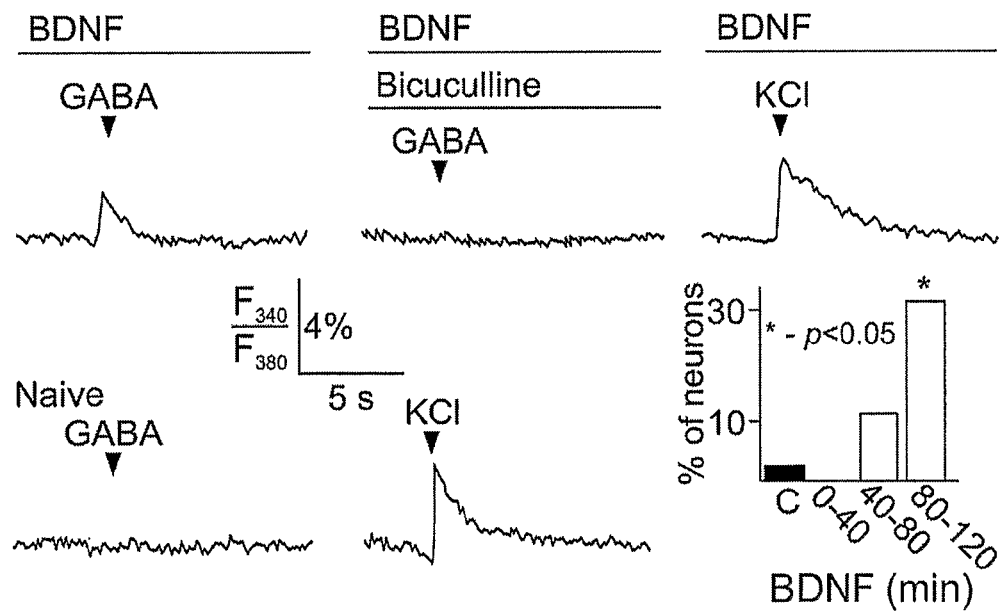

To determine whether BDNF could cause a shift in the $E_{anion}$, Applicant bath-applied it to spinal slices taken from naïve rats. Applicant found that $E_{anion}$ of LI neurons (n=9) in slices treated with BDNF (>90 min) was significantly less negative than that of LI neurons from control, untreated slices (n=9; $p<0.005$; FIG. 2B). Thus, it is possible that responses to GABA may be excitatory, rather than inhibitory, during BDNF administration. Applicant investigated this issue by monitoring the level of intracellular calcium ([$Ca^{2+}$]$_i$) following brief GABA applications in LI neurons (n=96) using calcium imaging. During perfusion with BDNF, and in the presence of glutamate receptor blockers, the proportion of neurons responding to GABA with a rise in [$Ca^{2+}$]$_i$ increased over time, reaching 31% of neurons recorded between 80-120 min ($p<0.05$; FIG. 2C). The rise in [$Ca^{2+}$]$_i$ was prevented by bath applying the GABA$_A$ receptor blocker bicuculline (n=18; $p<0.05$), confirming that the effect was mediated by GABA$_A$ receptors. Thus, Applicant concluded that acute administration of BDNF in slices caused a depolarizing shift in $E_{anion}$ and, in approximately 30% if the cells, caused GABA to produce net excitation.

To determine the effects of sustained, prolonged exposure to BDNF in vivo, Applicant administered a BDNF transducing recombinant adenovirus (adBDNF)[28] via an intrathecal catheter (n=16). This adBDNF caused a progressive decrease in paw withdrawal threshold over 4 days of post-injection testing. In contrast, injection of a control adenovirus, not encoding BDNF had no effect on paw withdrawal threshold over the same period (n=6; $p<0.005$; FIG. 2D). Because of the prolonged effect of the adBDNF treatment, Applicant was able to test for changes in $E_{anion}$ in slices taken from treated animals. Applicant found that $E_{anion}$ in LI neurons from adBDNF-injected rats (n=7) was significantly less negative than $E_{anion}$ measured from rats treated with the control adenovirus (n=4; $p<0.01$; FIGS. 2E,F). Moreover, GABA application caused some LI neurons from adBDNF-injected rats to fire action potentials (2 of 7 cells tested), whereas this was never observed in control conditions. Thus, like acute administration of BDNF, sustained local release caused a decrease in paw withdrawal threshold, a depolarizing shift in $E_{anion}$ and could switch the action of GABA from inhibitory to excitatory.

Figure 3C:
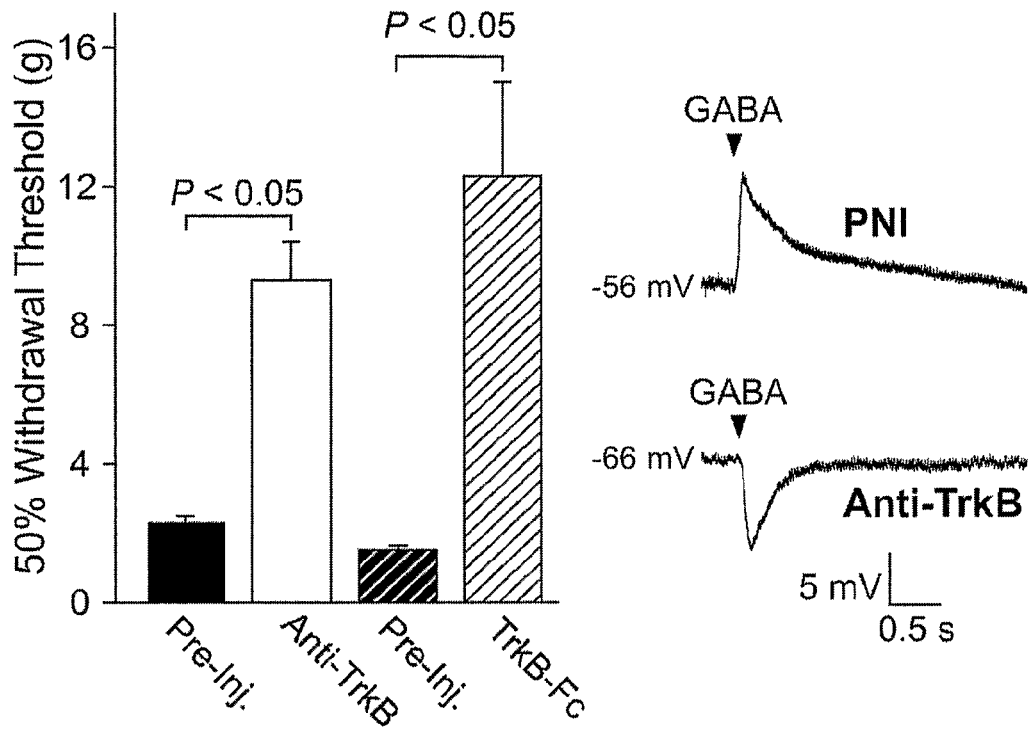
FIG. 3. Functional inhibition of BDNF-TrkB signalling reversed allodynia and the depolarizing shift in $E_{anion}$ in spinal lamina I neurons in rats with peripheral nerve injury. A, Intrathecal administration of either anti-TrkB or TrkB-Fc to the lumbar dorsal horn of rats that displayed a robust allodynia in response to peripheral nerve injury (PNI) caused a significant increase in the $WD_{50}$. B, Representative traces, in current clamp recording mode, illustrating that the postsynaptic response to GABA were depolarizing from rest in LI neurons taken from PNI rats, whereas these potentials were hyperpolarizing from rest in slices perfused with anti-TrkB. C, Representative current-voltage plots, in voltage clamp recording mode, of responses to brief local GABA applications (10 ms) in two LI neurons in slices taken from PNI rats, one taken from a slice superfused with control ACSF (control), the other taken from a slice after 2 hour of anti-TrkB perfusion (1 μg/ml). Inset, Pooled data showing that anti-TrkB perfusion of slices taken from rats that had received PNI elicited a significant hyperpolarization of $E_{anion}$ in LI neurons.
Figure 3C:
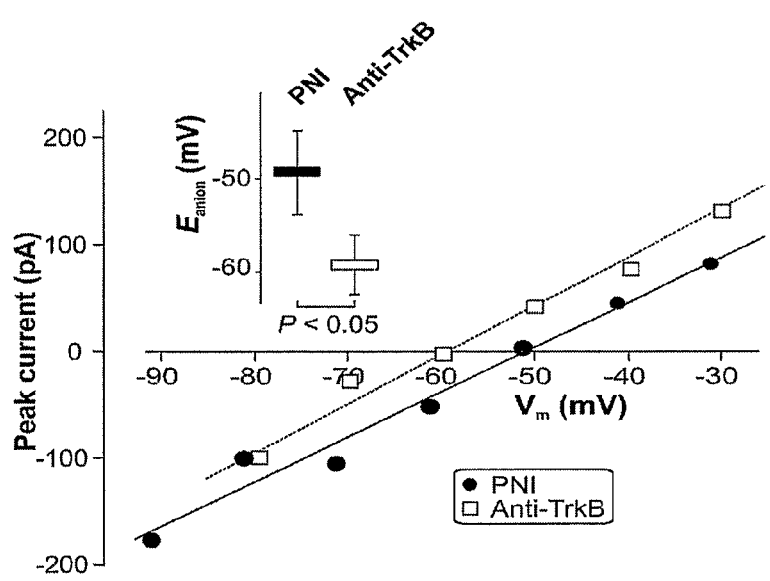

These results show that exogenous BDNF is sufficient to cause tactile allodynia and a shift in $E_{anion}$. To investigate whether BDNF might be an endogenous mediator of the sequelae of peripheral nerve injury, Applicant used a function-blocking antibody against the TrkB receptor (anti-TrkB) as well as a BDNF sequestering fusion protein (TrkB-Fc), each of which has been demonstrated to block the effects of BDNF[5,25,29]. Applicant administered anti-TrkB or TrkB-Fc by intrathecal catheter to rats that had developed allodynia two weeks after peripheral nerve injury. Paw withdrawal threshold was measured before and after administration of these agents. Applicant found that, each of these agents acutely reversed the decrease in paw withdrawal threshold (n=7 & 4, respectively, $p<0.05$; FIG. 3A). In contrast, vehicle administration to rats with peripheral nerve injury produced no change in withdrawal threshold (FIG. 3A). To determine whether BDNF-TrkB signalling is necessary for the nerve injury induced shift in $E_{anion}$ in LI neurons, Applicant examined the effect of anti-TrkB applied acutely to spinal cord slices taken from rats with allodynia two weeks after peripheral nerve injury. Applicant found that $E_{anion}$ of LI neurons in slices treated with anti-TrkB (n=7), was significantly more negative compared with $E_{anion}$ in vehicle-treated slices (n=6; $p<0.05$; FIGS. 3B,C). Taken together, these findings indicate that endogenous BDNF is necessary to sustain both the tactile allodynia and the depolarizing shift in $E_{anion}$ in LI neurons that result from peripheral nerve injury.

Figure 4D:
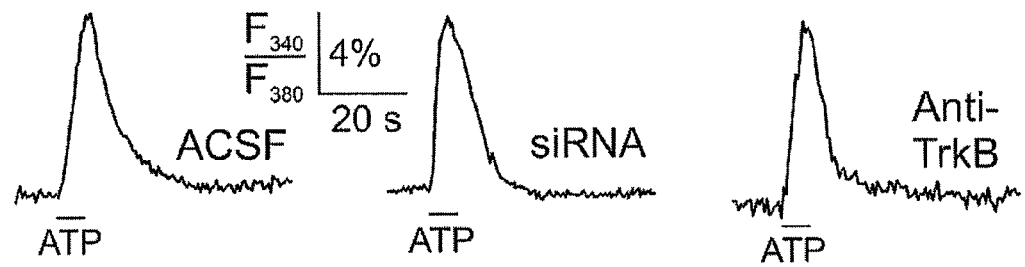
FIG. 4. Microglia-derived BDNF triggers both allodynia and the depolarizing shift in the transmembrane anion gradient of spinal lamina I neurons. A, Neither local spinal delivery of ATP-stimulated microglia incubated with anti-TrkB or TrkB-Fc, nor lipofected with BDNF interfering RNA (siRNA) caused a significant change in the paw withdrawal threshold ($WD_{50}$). Lipofection of ATP-stimulated microglia with a scrambled version of the interfering RNA (Scr. siRNA) did, however, cause the $WD_{50}$ to drop significantly after five hours. B, Representative traces, in current clamp recording mode, illustrating that postsynaptic responses to GABA were hyperpolarizing in LI neurons taken from rats treated with either ATP-stimulated microglia in combination with anti-TrkB, or ATP-stimulated microglia lipofected with BDNF siRNA. C, Pooled data showing that the mean $E_{anion}$ measured from LI neurons taken from rats that had received local spinal delivery of either ATP-stimulated microglia mixed with anti-TrkB or ATPstimulated microglia lipofected with BDNF siRNA was significantly more negative than that measured from LI neurons from rats that were injected with ATP-stimulated microglia. D, Representative traces of calcium measurements from Fura-2-AM-loaded microglia showing that responses of the cells to brief applications of ATP were not affected by exposure of microglia to anti-TrkB nor BDNF siRNA. E, ELISA-based measurement of BDNF protein in the supernatant of cultured microglia 5 hours after treatment with phosphate buffered saline vehicle (PBS), ATP, ATP+TNP-ATP (10 µM) or ATP after pre-treatment with BDNF siRNA. F, Correlation plot demonstrating the relationship between $E_{anion}$ and $WD_{50}$. The data in this plot includes only those where both $WD_{50}$ and $E_{anion}$ were recorded in the same rat.

To test whether interfering with BDNF-TrkB signalling should prevent the tactile allodynia and the shift in LI neuronal $E_{anion}$ produced by administering ATP-stimulated microglia, Applicant administered ATP stimulated microglia together with anti-TrkB or TrkB-Fc. Administering ATP-stimulated microglia together with either of these blockers led to no change in paw withdrawal threshold over the 5 hours after intrathecal injection (n=8 & 7, respectively; FIG. 4A). By contrast, allodynia developed progressively after administration of ATP-stimulated microglia without these agents (n=8). Microglia stimulated with ATP may provoke the release of BDNF from cells within the spinal cord. The blockers may interfere with the action of BDNF from this source rather than from the administered microglia per se. To differentiate between these two possibilities, Applicant pre-treated the cultured microglia with double-stranded RNA directed against BDNF (BDNF siRNA[6]). Following this pre-treatment, microglia were stimulated with ATP and, when injected intrathecally into naïve rats, failed to cause a change in withdrawal threshold (n=7; FIG. 4A). To control for possible non-specific effects of siRNA, Applicant treated microglia with a scrambled version of the BDNF siRNA prior to ATP stimulation; these microglia elicited a robust allodynia (n=4, FIG. 4A). Also, ATP-evoked calcium responses in the microglia treated with anti-TrkB or with BDNF siRNA were not different from those of vehicle-treated control microglia, demonstrating that the anti-TrkB or treatment with BDNF siRNA did not affect the response of the microglia to ATP (FIG. 4D). However, interfering with BDNF-TrkB signalling prevented microglia-induced tactile allodynia.

The depolarizing shift in $E_{anion}$ produced by ATP-stimulated microglia may be prevented by interfering with BDNF-TrkB signalling. Applicant found that $E_{anion}$ in LI neurons from animals receiving ATP-stimulated microglia together with anti-TrkB or after BDNF siRNA pre-treatment was not significantly different from that in LI neurons from animals receiving unstimulated microglia. However, the $E_{anion}$ in LI neurons taken from either of these groups of rats was significantly more negative compared with that of LI neurons taken from animals that had received ATP-stimulated microglia with vehicle (FIG. 4C). Thus, anti-TrkB and BDNF siRNA prevented the shift in $E_{anion}$ induced by ATP-stimulated microglia.

Figure 4E:
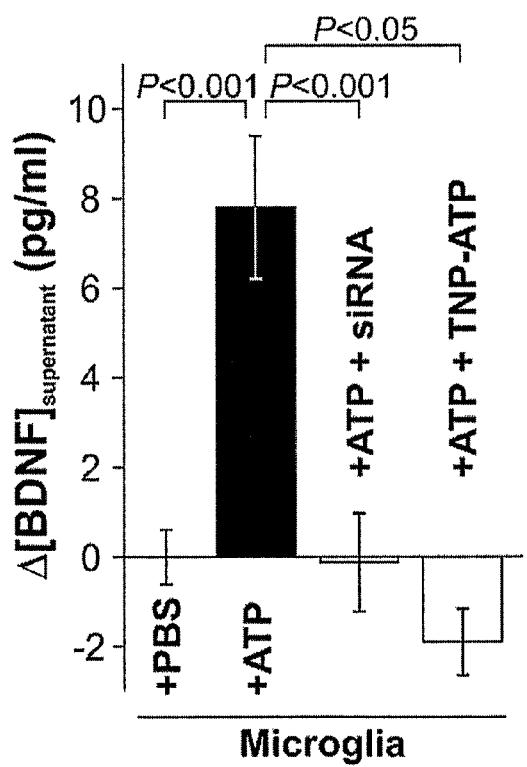

Moreover, ATP stimulation (n=3), but not vehicle control (n=4), caused release of BDNF from microglia in culture ($p<0.001$; FIG. 4E). This effect of ATP was blocked by treating the cultures with the P2X receptor blocker TNP-ATP (n=3; $p<0.05$). Additionally, pre-treatment of the microglia with the BDNF siRNA prevented release of BDNF by ATP stimulation (n=3; $p<0.001$). Taking these findings together with the behavioural and electrophysiological results above, Applicant concluded that both the decrease in paw withdrawal threshold and the shift in $E_{anion}$ in LI neurons caused by ATP-stimulated microglia requires BDNF-TrkB signalling and that the source of BDNF is the microglia themselves.

Figure 4F:
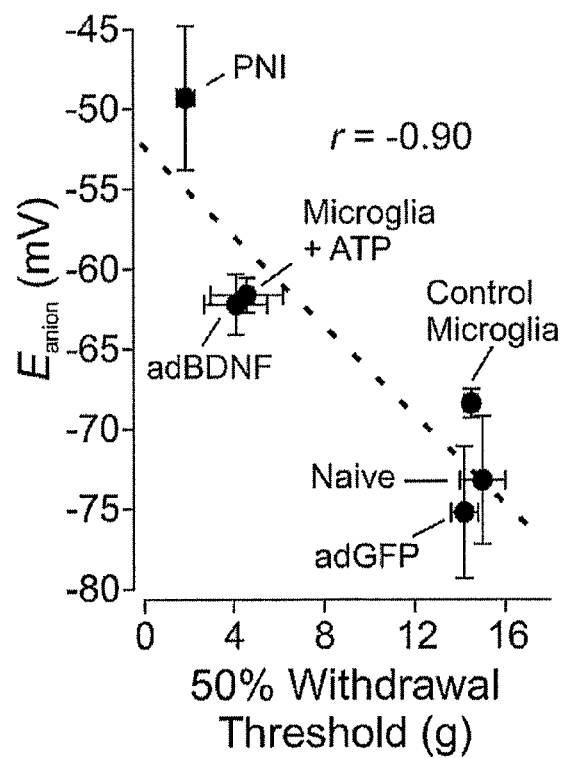

To test whether inhibiting microglial ATP signalling could suppress the shift in $E_{anion}$ caused by peripheral nerve injury, Applicant used TNP-ATP, which has been shown to reverse nerve injury-induced tactile allodynia by acting on P2X receptors in microglia[2]. Applicant bath-applied TNP-ATP acutely to spinal slices taken from allodynia rats two weeks after peripheral nerve injury. In the presence of TNP-ATP, the $E_{anion}$ of LI neurons was $-59.3\pm1.8$ mV (n=6), which was significantly more negative compared with that in LI neurons from untreated slices taken from nerve injured animals ($-49.3\pm4.5$ mV, n=6, $p<0.05$). Thus, Applicant concluded that P2X receptor activation is necessary to sustain the depolarised shift in $E_{anion}$ animals with peripheral nerve injury. Moreover, Applicant found an inverse correlation between paw withdrawal threshold and $E_{anion}$ in LI neurons across all experimental conditions (FIG. 4F), suggesting $E_{anion}$ as a critical mechanistic link between microglia and allodynia.

It is clear that BDNF of neuronal origin is required for the normal tuning of inhibitory synapses in the brain[14] and spinal cord[15]; indeed, patterns of stimulation known to trigger long-term postsynaptic plasticity have been demonstrated to elicit the release of BDNF from primary afferents in the superficial dorsal horn[11]. However, it appears that only brief activation of TrkB receptors is necessary for normal plasticity, as the application of BDNF sequestering antibodies has been documented to attenuate only the induction of long-term plasticity, having no effect on maintenance[16]. In contrast, the pathophysiological repression of inhibition may require the repetitive activation of TrkB receptors: TrkB inhibition by application of a neutralizing antibody (anti-TrkB) was shown here to rapidly attenuate pain hypersensitivity, as well as decreases in LI neuronal anion gradient—stemming from nerve injury. The studies described herein thus demonstrate the advantage of targeting microglia-derived BDNF for therapeutic intervention of neuropathic pain, rather than manipulating all BDNF action, because it represents a strategy to eliminate processes catalyzing the disease, while leaving intact processes critical for normal neuronal function (i.e. neuronal pools of BDNF). Therefore, in an embodiment, the methods described herein result in no or substantially no effects on normal neuronal processes.

Throughout this application, various references are referred to describe more fully the state of the art to which this invention pertains. The disclosures of these references are hereby incorporated by reference into the present disclosure.

REFERENCES

1. Woolf, C. J. & Salter, M. W. Neuronal plasticity: increasing the gain in pain. *Science* 288, 1765-1769 (2000).
2. Tsuda, M. et al. P2X4 receptors induced in spinal microglia gate tactile allodynia after nerve injury. *Nature* 424, 778-783 (2003).
3. Coull, J. A. et al. Trans-synaptic shift in anion gradient in spinal lamina I neurons as a mechanism of neuropathic pain. *Nature* 424, 938-942 (2003).
4. Thompson, S. W., Bennett, D. L., Kerr, B. J., Bradbury, E. J. & McMahon, S. B. Brain derived neurotrophic factor is an endogenous modulator of nociceptive responses in the spinal cord. *Proc. Natl. Acad. Sci. U.S.A* 96, 7714-7718 (1999).
5. Jiang, B., Akaneya, Y., Hata, Y. & Tsumoto, T. Long-term depression is not induced by low-frequency stimulation in rat visual cortex in vivo: a possible preventing role of endogenous brain-derived neurotrophic factor. *J. Neurosci.* 23, 3761-3770 (2003).
6. Baker-Herman, T. L. et al. BDNF is necessary and sufficient for spinal respiratory plasticity following intermittent hypoxia. *Nat. Neurosci.* 7, 48-55 (2004).
7. Yajima, Y., Narita, M., Narita, M., Matsumoto, N. & Suzuki, T. Involvement of a spinal brain-derived neurotrophic factor/full-length TrkB pathway in the development of nerve injury-induced thermal hyperalgesia in mice. *Brain Res.* 958, 338-346 (2002).
8. Kerr, B. J. et al. Brain-derived neurotrophic factor modulates nociceptive sensory inputs and NMDA-evoked responses in the rat spinal cord. *J Neurosci* 19, 5138-5148 (1999).
9. Miletic, G. & Miletic, V. Increases in the concentration of brain derived neurotrophic factor in the lumbar spinal dorsal horn are associated with pain behavior following chronic constriction injury in rats. *Neurosci Lett* 319, 137-140 (2002).
10. Dougherty, K. D., Dreyfus, C. F. & Black, I. B. Brain-derived neurotrophic factor in astrocytes, oligodendrocytes, and microglia/macrophages after spinal cord injury. *Neurobiol. Dis.* 7, 574-585 (2000).
11. Lever, I. J. et al. Brain-derived neurotrophic factor is released in the dorsal horn by distinctive patterns of afferent fiber stimulation. *J. Neurosci.* 21, 4469-4477 (2001).
12. Moriguchi, S. et al. Potentiation of NMDA receptor-mediated synaptic responses by microglia. *Brain Res. Mol. Brain. Res.* 119, 160-169 (2003).
13. Groth, R. & Aanonsen, L. Spinal brain-derived neurotrophic factor (BDNF) produces hyperalgesia in normal mice while antisense directed against either BDNF or trkB, prevent inflammation-induced hyperalgesia. *Pain* 100, 171-181 (2002).
14. Wardle, R. A. & Poo, M. M. Brain-derived neurotrophic factor modulation of GABAergic synapses by postsynaptic regulation of chloride transport. *J. Neurosci.* 23, 8722-8732 (2003).
15. Skup, M. et al. Long-term locomotor training up-regulates TrkB(FL) receptor-like proteins, brain-derived neu- 16. Chen, G., Kolbeck, R., Barde, Y. A., Bonhoeffer, T. & Kossel, A. Relative contribution of endogenous neurotrophins in hippocampal long-term potentiation. *J. Neurosci.* 19, 7983-7990 (1999).
17. Mosconi, T. & Kruger, L. Fixed-diameter polyethylene cuffs applied to the rat sciatic nerve induce a painful neuropathy: ultrastructural morphometric analysis of axonal alterations. *Pain* 64, 37-57 (1996).
18. Chaplan, S. R., Bach, F. W., Pogrel, J. W., Chung, J. M. & Yaksh, T. L. Quantitative assessment of tactile allodynia in the rat paw. *J Neurosci Methods* 53, 55-63 (1994).
19. Keller, A. F., Coull, J. A., Chery, N., Poisbeau, P. & de Koninck, Y. Region-specific developmental specialization of GABA-glycine cosynapses in laminas I-II of the rat spinal dorsal horn. *J Neurosci* 21, 7871-7880 (2001).
20. Tyzio, R. et al. Membrane potential of CA3 hippocampal pyramidal cells during postnatal development. *J. Neurophysiol.* 90, 2964-2972 (2003).
21. Nakajima, K. et al. Identification of elastase as a secretory protease from cultured rat microglia. *J. Neurochem.* 58, 1401-1408 (1992).
22. Yaksh, T. L., Jessell, T. M., Gamse, R., Mudge, A. W. & Leeman, S. E. Intrathecal morphine inhibits substance P release from mammalian spinal cord in vivo. *Nature* 286, 155-157 (1980).
23. Coderre, T. J. & Melzack, R. The contribution of excitatory amino acids to central sensitization and persistent nociception after formalin-induced tissue injury. *J Neurosci* 12, 3665-3670 (1992).
24. Nakajima, K., Tohyama, Y., Kohsaka, S. & Kurihara, T. Ceramide activates microglia to enhance the production/secretion of brain-derived neurotrophic factor (BDNF) without induction of deleterious factors in vitro. *J. Neurochem.* 80, 697-705 (2002).
25. Mannion, R. J. et al. Neurotrophins: peripherally and centrally acting modulators of tactile stimulus-induced inflammatory pain hypersensitivity. *Proc. Natl. Acad. Sci. U.S.A.* 96, 9385-9390 (1999).
26. Heppenstall, P. A. & Lewin, G. R. BDNF but not NT-4 is required for normal flexion reflex plasticity and function. *Proc. Natl. Acad. Sci. U.S.A.* 98, 8107-8112 (2001).
27. Rivera, C. et al. BDNF-induced TrkB activation down-regulates the K+–Cl– cotransporter KCC2 and impairs neuronal Cl– extrusion. *J. Cell Biol.* 159, 747-752 (2002).
28. Gravel, C., Gotz, R., Lorrain, A. & Sendtner, M. Adenoviral gene transfer of ciliary neurotrophic factor and brain-derived neurotrophic factor leads to long-term survival of axotomized motor neurons. *Nat. Med.* 3, 765-770 (1997).
29. Balkowiec, A. & Katz, D. M. Activity-dependent release of endogenous brain-derived neurotrophic factor from primary sensory neurons detected by ELISA in situ. *J. Neurosci.* 20, 7417-7423 (2000).
30. Malcangio, M. & Lessmann, V. A common thread for pain and memory synapses? Brain derived neurotrophic factor and trkB receptors. *Trends Pharmacol. Sci.* 24, 116-121 (2003).
31. Chery, N., Yu, X. H. & De Koninck, Y. Visualization of lamina I of the dorsal horn in live adult rat spinal cord slices. *J Neurosci Methods* 96, 133-142 (2000).

What is claimed is:

1. A method of identifying a compound for the treatment or prevention of pain, said method comprising:
   (a) contacting said compound with a neuroglia expressing, releasing or secreting BDNF in vitro, in the absence of neuronal cells;
   (b) determining whether said test compound decreases BDNF expression, release or secretion in said neuroglia; and
   (c) if said test compound decreases BDNF expression, release or secretion in said neuroglia, determining whether said test compound treats or prevents pain in an animal.

2. The method of claim 1, wherein said neuroglia is a stimulated neuroglia.

3. The method of claim 2, wherein said stimulated neuroglia has been contacted with ATP prior to step (a).

4. The method of claim 1, wherein said neuroglia is selected from the group consisting of a microglia, an astrocyte and an oligodendrocyte.

5. The method of claim 1, wherein said test compound is selected from the group consisting of a dsRNA, a siRNA, a siRNA-like molecule, an antisense oligonucleotide and a ribozyme.

6. The method of claim 1, wherein said animal is a rat.

* * * * *

SEQUENCE LISTING

```
<160> NUMBER OF SEQ ID NOS: 10

<210> SEQ ID NO 1
<211> LENGTH: 918
<212> TYPE: DNA
<213> ORGANISM: Homo sapiens
<220> FEATURE:
<221> NAME/KEY: CDS
<222> LOCATION: (76)..(816)

<400> SEQUENCE: 1
ggtgaaagaa agccctaacc agttttctgt cttgtttctg ctttctccct acagttccac      60
caggtgagaa gagtg atg acc atc ctt ttc ctt act atg gtt att tca tac     111
                Met Thr Ile Leu Phe Leu Thr Met Val Ile Ser Tyr
                  1               5                  10 ttt ggt tgc atg aag gct gcc ccc atg aaa gaa gca aac atc cga gga     159
Phe Gly Cys Met Lys Ala Ala Pro Met Lys Glu Ala Asn Ile Arg Gly
             15                  20                  25 caa ggt ggc ttg gcc tac cca ggt gtg cgg acc cat ggg act ctg gag     207
Gln Gly Gly Leu Ala Tyr Pro Gly Val Arg Thr His Gly Thr Leu Glu
         30                  35                  40 agc gtg aat ggg ccc aag gca ggt tca aga ggc ttg aca tca ttg gct     255
Ser Val Asn Gly Pro Lys Ala Gly Ser Arg Gly Leu Thr Ser Leu Ala
 45                  50                  55                  60 gac act ttc gaa cac gtg ata gaa gag ctg ttg gat gag gac cag aaa     303
Asp Thr Phe Glu His Val Ile Glu Glu Leu Leu Asp Glu Asp Gln Lys
                 65                  70                  75 gtt cgg ccc aat gaa gaa aac aat aag gac gca gac ttg tac acg tcc     351
Val Arg Pro Asn Glu Glu Asn Asn Lys Asp Ala Asp Leu Tyr Thr Ser
```

```
                        80                  85                  90
agg gtg atg ctc agt agt caa gtg cct ttg gag cct cct ctt ctc ttt      399
Arg Val Met Leu Ser Ser Gln Val Pro Leu Glu Pro Pro Leu Leu Phe
            95                  100                 105 ctg ctg gag gaa tac aaa aat tac cta gat gct gca aac atg tcc atg      447
Leu Leu Glu Glu Tyr Lys Asn Tyr Leu Asp Ala Ala Asn Met Ser Met
110                 115                 120 agg gtc cgg cgc cac tct gac cct gcc cgc cga ggg gag ctg agc gtg      495
Arg Val Arg Arg His Ser Asp Pro Ala Arg Arg Gly Glu Leu Ser Val
125                 130                 135                 140 tgt gac agt att agt gag tgg gta acg gcg gca gac aaa aag act gca      543
Cys Asp Ser Ile Ser Glu Trp Val Thr Ala Ala Asp Lys Lys Thr Ala
            145                 150                 155 gtg gac atg tcg ggc ggg acg gtc aca gtc ctt gaa aag gtc cct gta      591
Val Asp Met Ser Gly Gly Thr Val Thr Val Leu Glu Lys Val Pro Val
        160                 165                 170 tca aaa ggc caa ctg aag caa tac ttc tac gag acc aag tgc aat ccc      639
Ser Lys Gly Gln Leu Lys Gln Tyr Phe Tyr Glu Thr Lys Cys Asn Pro
        175                 180                 185 atg ggt tac aca aaa gaa ggc tgc agg ggc ata gac aaa agg cat tgg      687
Met Gly Tyr Thr Lys Glu Gly Cys Arg Gly Ile Asp Lys Arg His Trp
    190                 195                 200 aac tcc cag tgc cga act acc cag tcg tac gtg cgg gcc ctt acc atg      735
Asn Ser Gln Cys Arg Thr Thr Gln Ser Tyr Val Arg Ala Leu Thr Met
205                 210                 215                 220 gat agc aaa aag aga att ggc tgg cga ttc ata agg ata gac act tct      783
Asp Ser Lys Lys Arg Ile Gly Trp Arg Phe Ile Arg Ile Asp Thr Ser
            225                 230                 235 tgt gta tgt aca ttg acc att aaa agg gga aga tagtggattt atgttgtata    836
Cys Val Cys Thr Leu Thr Ile Lys Arg Gly Arg
        240                 245 gattagatta tattgagaca aaaattatct atttgtatat atacataaca gggtaaatta    896
ttcagttaag aaaaaaataa tt                                             918

<210> SEQ ID NO 2
<211> LENGTH: 247
<212> TYPE: PRT
<213> ORGANISM: Homo sapiens

<400> SEQUENCE: 2

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140
```

```
Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Lys Cys Asn Pro Met Gly Tyr Thr
        180                 185                 190

Lys Glu Gly Cys Arg Gly Ile Asp Lys Arg His Trp Asn Ser Gln Cys
    195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 3
<211> LENGTH: 1158
<212> TYPE: DNA
<213> ORGANISM: Mus musculus
<220> FEATURE:
<221> NAME/KEY: CDS
<222> LOCATION: (28)..(774)

<400> SEQUENCE: 3
cctgagttcc accaggtgag aagagtg atg acc atc ctt ttc ctt act atg gtt      54
                              Met Thr Ile Leu Phe Leu Thr Met Val
                                1               5 att tca tac ttc ggt tgc atg aag gcg gcg ccc atg aaa gaa gta aac      102
Ile Ser Tyr Phe Gly Cys Met Lys Ala Ala Pro Met Lys Glu Val Asn
 10              15                  20                  25 gtc cac gga caa ggc aac ttg gcc tac cca ggt gtg cgg acc cat ggg      150
Val His Gly Gln Gly Asn Leu Ala Tyr Pro Gly Val Arg Thr His Gly
                 30                  35                  40 act ctg gag agc gtg aat ggg ccc agg gca ggt tcg aga ggt ctg acg      198
Thr Leu Glu Ser Val Asn Gly Pro Arg Ala Gly Ser Arg Gly Leu Thr
             45                  50                  55 acg aca tca ctg gct gac act ttt gag cac gtc atc gaa gag ctg ctg      246
Thr Thr Ser Leu Ala Asp Thr Phe Glu His Val Ile Glu Glu Leu Leu
         60                  65                  70 gat gag gac cag aag gtt cgg ccc aac gaa gaa aac cat aag gac gcg      294
Asp Glu Asp Gln Lys Val Arg Pro Asn Glu Glu Asn His Lys Asp Ala
 75                  80                  85 gac ttg tac act tcc cgg gtg atg ctc agc agt caa gtg cct ttg gag      342
Asp Leu Tyr Thr Ser Arg Val Met Leu Ser Ser Gln Val Pro Leu Glu
 90                  95                 100                 105 cct cct cta ctc ttt ctg ctg gag gaa tac aaa aat tac ctg gat gcc      390
Pro Pro Leu Leu Phe Leu Leu Glu Glu Tyr Lys Asn Tyr Leu Asp Ala
                110                 115                 120 gca aac atg tct atg agg gtt cgg cgc cac tcc gac cct gcc cgc cgt      438
Ala Asn Met Ser Met Arg Val Arg Arg His Ser Asp Pro Ala Arg Arg
            125                 130                 135 ggg gag ctg agc gtg tgt gac agt att agc gag tgg gtc aca gcg gca      486
Gly Glu Leu Ser Val Cys Asp Ser Ile Ser Glu Trp Val Thr Ala Ala
        140                 145                 150 gat aaa aag act gca gtg gac atg tct ggc ggg acg gtc aca gtc cta      534
Asp Lys Lys Thr Ala Val Asp Met Ser Gly Gly Thr Val Thr Val Leu
    155                 160                 165 gag aaa gtc ccg gta tcc aaa ggc caa ctg aag cag tat ttc tac gag      582
Glu Lys Val Pro Val Ser Lys Gly Gln Leu Lys Gln Tyr Phe Tyr Glu
170                 175                 180                 185
```

| | | | | | | | | | | | | | | | | |
|---|---|---|---|---|---|---|---|---|---|---|---|---|---|---|---|---|
| acc | aag | tgt | aat | ccc | atg | ggt | tac | acc | aag | gaa | ggc | tgc | agg | ggc | ata | 630 |
| Thr | Lys | Cys | Asn | Pro | Met | Gly | Tyr | Thr | Lys | Glu | Gly | Cys | Arg | Gly | Ile | |
| | | | 190 | | | | | 195 | | | | | 200 | | | |
| gac | aaa | agg | cac | tgg | aac | tcg | caa | tgc | cga | act | acc | caa | tcg | tat | gtt | 678 |
| Asp | Lys | Arg | His | Trp | Asn | Ser | Gln | Cys | Arg | Thr | Thr | Gln | Ser | Tyr | Val | |
| | 205 | | | | | 210 | | | | | 215 | | | | | |
| cgg | gcc | ctt | act | atg | gat | agc | aaa | aag | aga | att | ggc | tgg | cga | ttc | ata | 726 |
| Arg | Ala | Leu | Thr | Met | Asp | Ser | Lys | Lys | Arg | Ile | Gly | Trp | Arg | Phe | Ile | |
| | 220 | | | | | 225 | | | | | 230 | | | | | |
| agg | ata | gac | act | tcc | tgt | gta | tgt | aca | ctg | acc | att | aaa | agg | gga | aga | 774 |
| Arg | Ile | Asp | Thr | Ser | Cys | Val | Cys | Thr | Leu | Thr | Ile | Lys | Arg | Gly | Arg | |
| | 235 | | | | | 240 | | | | | 245 | | | | | |

```
tagtggattt atgttgtata gattatattg agacaaaatt atctatttgt atatatacat      834
aacagggtaa attattcagt taagaaaaaa taattttatg aactgcatgt ataaatgaag      894
tttatacagt acagtggttc tacaatctat ttattggaca tatccatgac ctgaaaggaa      954
acagtcattt gcgcacaact ttaaaagtct gcattacatt cctcgataat gttgtggttt     1014
gttgccgttg ccaagaattg aaaacaaaaa gtttaaaaaa aataataata aattgcatgc     1074
tgctttaatt gtgaattgat aataaactgt ccctctttca gaaaacagat taaaaaaaca     1134
aaaaaaaaaa aaaaaaaaaa aaaa                                           1158

<210> SEQ ID NO 4
<211> LENGTH: 249
<212> TYPE: PRT
<213> ORGANISM: Mus musculus

<400> SEQUENCE: 4
```

| | | | | | | | | | | | | | | |
|---|---|---|---|---|---|---|---|---|---|---|---|---|---|---|
| Met | Thr | Ile | Leu | Phe | Leu | Thr | Met | Val | Ile | Ser | Tyr | Phe | Gly | Cys | Met |
| 1 | | | | 5 | | | | | 10 | | | | | 15 |
| Lys | Ala | Ala | Pro | Met | Lys | Glu | Val | Asn | Val | His | Gly | Gln | Gly | Asn | Leu |
| | | | 20 | | | | | 25 | | | | | 30 | |
| Ala | Tyr | Pro | Gly | Val | Arg | Thr | His | Gly | Thr | Leu | Glu | Ser | Val | Asn | Gly |
| | | 35 | | | | | 40 | | | | | 45 | | |
| Pro | Arg | Ala | Gly | Ser | Arg | Gly | Leu | Thr | Thr | Thr | Ser | Leu | Ala | Asp | Thr |
| | 50 | | | | | 55 | | | | | 60 | | | |
| Phe | Glu | His | Val | Ile | Glu | Glu | Leu | Leu | Asp | Glu | Asp | Gln | Lys | Val | Arg |
| 65 | | | | | 70 | | | | | 75 | | | | | 80 |
| Pro | Asn | Glu | Glu | Asn | His | Lys | Asp | Ala | Asp | Leu | Tyr | Thr | Ser | Arg | Val |
| | | | | 85 | | | | | 90 | | | | | 95 |
| Met | Leu | Ser | Ser | Gln | Val | Pro | Leu | Glu | Pro | Pro | Leu | Leu | Phe | Leu | Leu |
| | | | 100 | | | | | 105 | | | | | 110 | |
| Glu | Glu | Tyr | Lys | Asn | Tyr | Leu | Asp | Ala | Ala | Asn | Met | Ser | Met | Arg | Val |
| | | 115 | | | | | 120 | | | | | 125 | | |
| Arg | Arg | His | Ser | Asp | Pro | Ala | Arg | Arg | Gly | Glu | Leu | Ser | Val | Cys | Asp |
| | 130 | | | | | 135 | | | | | 140 | | | |
| Ser | Ile | Ser | Glu | Trp | Val | Thr | Ala | Ala | Asp | Lys | Lys | Thr | Ala | Val | Asp |
| 145 | | | | | 150 | | | | | 155 | | | | | 160 |
| Met | Ser | Gly | Gly | Thr | Val | Thr | Val | Leu | Glu | Lys | Val | Pro | Val | Ser | Lys |
| | | | | 165 | | | | | 170 | | | | | 175 |
| Gly | Gln | Leu | Lys | Gln | Tyr | Phe | Tyr | Glu | Thr | Lys | Cys | Asn | Pro | Met | Gly |
| | | | 180 | | | | | 185 | | | | | 190 | |
| Tyr | Thr | Lys | Glu | Gly | Cys | Arg | Gly | Ile | Asp | Lys | Arg | His | Trp | Asn | Ser |
| | | 195 | | | | | 200 | | | | | 205 | | |
| Gln | Cys | Arg | Thr | Thr | Gln | Ser | Tyr | Val | Arg | Ala | Leu | Thr | Met | Asp | Ser |
| | 210 | | | | | 215 | | | | | 220 | | | |

```
Lys Lys Arg Ile Gly Trp Arg Phe Ile Arg Ile Asp Thr Ser Cys Val
225                 230                 235                 240

Cys Thr Leu Thr Ile Lys Arg Gly Arg
                245

<210> SEQ ID NO 5
<211> LENGTH: 750
<212> TYPE: DNA
<213> ORGANISM: Rattus norvegicus
<220> FEATURE:
<221> NAME/KEY: CDS
<222> LOCATION: (1)..(747)

<400> SEQUENCE: 5 atg acc atc ctt ttc ctt act atg gtt att tca tac ttc ggt tgc atg      48
Met Thr Ile Leu Phe Leu Thr Met Val Ile Ser Tyr Phe Gly Cys Met
1               5                   10                  15 aag gct gcg ccc atg aaa gaa gca aac gtc cac gga caa ggc aac ttg      96
Lys Ala Ala Pro Met Lys Glu Ala Asn Val His Gly Gln Gly Asn Leu
                20                  25                  30 gcc tac cca gct gtg cgg acc cat ggg act ctg gag agc gtg aat ggg     144
Ala Tyr Pro Ala Val Arg Thr His Gly Thr Leu Glu Ser Val Asn Gly
            35                  40                  45 ccc agg gca ggt tcg aga ggt ctg acg acg acg tcc ctg gct gac act     192
Pro Arg Ala Gly Ser Arg Gly Leu Thr Thr Thr Ser Leu Ala Asp Thr
50                  55                  60 ttt gag cac gtg atc gaa gag ctg ctg gat gag gac cag aag gtt cgg     240
Phe Glu His Val Ile Glu Glu Leu Leu Asp Glu Asp Gln Lys Val Arg
65                  70                  75                  80 ccc aac gaa gaa aac cat aag gac gcg gac ttg tac act tcc cgg gtg     288
Pro Asn Glu Glu Asn His Lys Asp Ala Asp Leu Tyr Thr Ser Arg Val
                85                  90                  95 atg ctc agc agt caa gtg cct ttg gag cct cct ctg ctc ttt ctg ctg     336
Met Leu Ser Ser Gln Val Pro Leu Glu Pro Pro Leu Leu Phe Leu Leu
            100                 105                 110 gag gaa tac aaa aat tac ctg gat gcc gca aac atg tct atg agg gtt     384
Glu Glu Tyr Lys Asn Tyr Leu Asp Ala Ala Asn Met Ser Met Arg Val
        115                 120                 125 cgg cgc cac tcc gac ccc gcc cgc cgt ggg gag ctg agc gtg tgt gac     432
Arg Arg His Ser Asp Pro Ala Arg Arg Gly Glu Leu Ser Val Cys Asp
    130                 135                 140 agt att agt gag tgg gta acg gcg gca gac aaa aag act gca gtg gac     480
Ser Ile Ser Glu Trp Val Thr Ala Ala Asp Lys Lys Thr Ala Val Asp
145                 150                 155                 160 atg tcg ggc ggg acg gtc aca gtc ctt gaa aag gtc cct gta tca aaa     528
Met Ser Gly Gly Thr Val Thr Val Leu Glu Lys Val Pro Val Ser Lys
                165                 170                 175 ggc caa ctg aag caa tac ttc tac gag acc aag tgc aat ccc atg ggt     576
Gly Gln Leu Lys Gln Tyr Phe Tyr Glu Thr Lys Cys Asn Pro Met Gly
            180                 185                 190 tac aca aaa gaa ggc tgc agg ggc ata gac aaa agg cat tgg aac tcc     624
Tyr Thr Lys Glu Gly Cys Arg Gly Ile Asp Lys Arg His Trp Asn Ser
        195                 200                 205 cag tgc cga act acc cag tcg tac gtg cgg gcc ctt acc atg gat agc     672
Gln Cys Arg Thr Thr Gln Ser Tyr Val Arg Ala Leu Thr Met Asp Ser
    210                 215                 220 aaa aag aga att ggc tgg cga ttc ata agg ata gac act tct tgt gta     720
Lys Lys Arg Ile Gly Trp Arg Phe Ile Arg Ile Asp Thr Ser Cys Val
225                 230                 235                 240 tgt aca ttg acc att aaa agg gga aga tag                              750
Cys Thr Leu Thr Ile Lys Arg Gly Arg
```

<210> SEQ ID NO 6
<211> LENGTH: 249
<212> TYPE: PRT
<213> ORGANISM: Rattus norvegicus

<400> SEQUENCE: 6

```
Met Thr Ile Leu Phe Leu Thr Met Val Ile Ser Tyr Phe Gly Cys Met
  1               5                  10                  15

Lys Ala Ala Pro Met Lys Glu Ala Asn Val His Gly Gln Gly Asn Leu
             20                  25                  30

Ala Tyr Pro Ala Val Arg Thr His Gly Thr Leu Glu Ser Val Asn Gly
         35                  40                  45

Pro Arg Ala Gly Ser Arg Gly Leu Thr Thr Thr Ser Leu Ala Asp Thr
     50                  55                  60

Phe Glu His Val Ile Glu Glu Leu Leu Asp Glu Asp Gln Lys Val Arg
 65                  70                  75                  80

Pro Asn Glu Glu Asn His Lys Asp Ala Asp Leu Tyr Thr Ser Arg Val
                 85                  90                  95

Met Leu Ser Ser Gln Val Pro Leu Glu Pro Pro Leu Leu Phe Leu Leu
            100                 105                 110

Glu Glu Tyr Lys Asn Tyr Leu Asp Ala Ala Asn Met Ser Met Arg Val
        115                 120                 125

Arg Arg His Ser Asp Pro Ala Arg Arg Gly Glu Leu Ser Val Cys Asp
    130                 135                 140

Ser Ile Ser Glu Trp Val Thr Ala Ala Asp Lys Lys Thr Ala Val Asp
145                 150                 155                 160

Met Ser Gly Gly Thr Val Thr Val Leu Glu Lys Val Pro Val Ser Lys
                165                 170                 175

Gly Gln Leu Lys Gln Tyr Phe Tyr Glu Thr Lys Cys Asn Pro Met Gly
            180                 185                 190

Tyr Thr Lys Glu Gly Cys Arg Gly Ile Asp Lys Arg His Trp Asn Ser
        195                 200                 205

Gln Cys Arg Thr Thr Gln Ser Tyr Val Arg Ala Leu Thr Met Asp Ser
    210                 215                 220

Lys Lys Arg Ile Gly Trp Arg Phe Ile Arg Ile Asp Thr Ser Cys Val
225                 230                 235                 240

Cys Thr Leu Thr Ile Lys Arg Gly Arg
                245
```

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
tcgaagagct gctggatga                                                   19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8

```
tatgtacact gaccattaa                                                 19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gagcgtgtgt gacagtatt                                                 19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
gaactaccca atcgtatgt                                                 19
```